United States Patent

Coles et al.

[11] Patent Number: 5,470,756
[45] Date of Patent: Nov. 28, 1995

[54] GAS SENSORS

[75] Inventors: Gary S. V. Coles; Geraint Williams, both of Swansea, United Kingdom

[73] Assignee: British Gas plc, London, England

[21] Appl. No.: 949,847

[22] PCT Filed: Mar. 15, 1991

[86] PCT No.: PCT/GB91/00400
   § 371 Date: Nov. 19, 1992
   § 102(e) Date: Nov. 19, 1992

[87] PCT Pub. No.: WO91/14939
   PCT Pub. Date: Oct. 3, 1991

[30] Foreign Application Priority Data

Mar. 19, 1990 [GB] United Kingdom ............ 90 06176

[51] Int. Cl.$^6$ .......................................... G01N 33/00
[52] U.S. Cl. .................... 436/144; 422/88; 422/90; 422/98
[58] Field of Search ................. 422/83, 88, 90, 422/98; 436/144

[56] References Cited

U.S. PATENT DOCUMENTS 5,185,130  2/1993  Camonzi et al. .................. 422/90

Primary Examiner—David A. Redding
Attorney, Agent, or Firm—William R. Hinds

[57] ABSTRACT $SnO_2$ gas sensors are described incorporating $Bi_2O_3$ in an amount less than 35% but sufficient to confer hydrogen sensitivity and selectivity to the sensors described comprises 25% by weight $Bi_2O_3$ and incorporates a platinum catalyst.

12 Claims, 5 Drawing Sheets

Gas Sensor Substrate

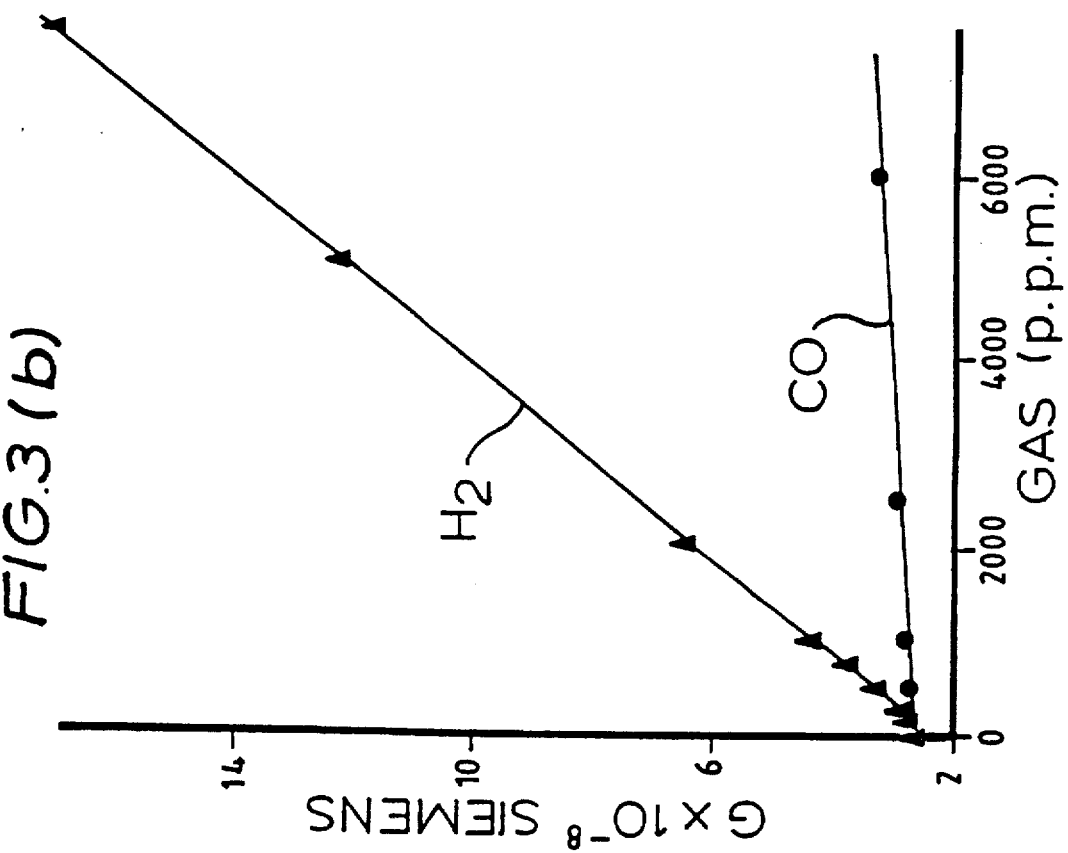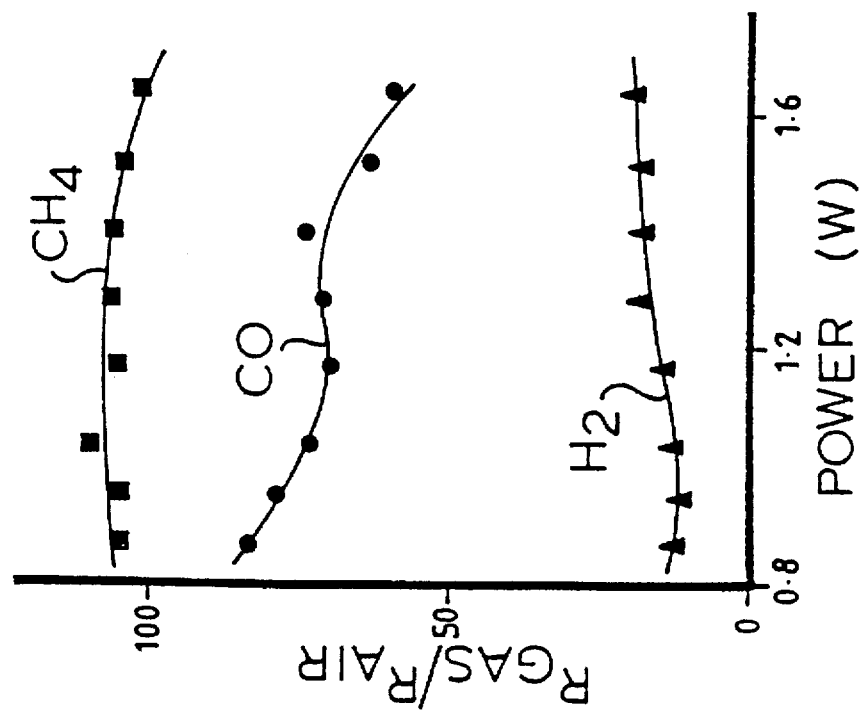

GAS SENSORS

TECHNICAL FIELD

This invention relates to gas sensors. In particular to hydrogen sensors.

BACKGROUND OF THE INVENTION

Extensive recent research into devices for the detection of inflammable or toxic gas in air has been centred on tin(IV) oxide ($SnO_2$) based thick film or sintered powder type sensors, these are commonly referred to as $SnO_2$ gas sensors. The mechanism of operation of such transducers relies on the conductivity changes experienced by the n-type semiconducting material when surface chemisorbed oxygen reacts with reducing gases such as carbon monoxide (CO) or methane ($CH_4$) at elevated temperatures. For carbon monoxide the overall reactions occurring on the $SnO_2$ surface can be written simply:

  (1)

  (2)

where $e^-$ represents a conduction band electron. In the absence of reducing gas (e.g. CO), electrons are removed from the semiconductor conduction band via the reduction of molecular oxygen, leading to a build-up of O– species and consequently the $SnO_2$ becomes very resistive. When CO is introduced, it undergoes oxidation to $CO_2$ by surface oxygen species and subsequently electrons are re-introduced into the conduction band leading to a decrease in this resistance.

The main advantages of $SnO_2$ based sensors include high sensitivity, low cost, fast response speed and low power consumption. However, there are also significant drawbacks such as long term drift and ambient humidity and temperature effects associated with such devices. Attempts have been made to overcome this last effect by operating these devices under very accurately temperature-controlled conditions though it is important to recognise that it is the surface and not the bulk temperature which controls the response. Another problem with $SnO_2$ based sensors is their relative lack of selectivity, since the chemisorbed oxygen (responsible for controlling surface conductivity) reacts with a wide range of reducing gases. Several approaches have been investigated with a view to enhancing specificity, including the use of filters or specific surface additives. These, along with other methods outlined briefly below have been reviewed recently by Morrison (Sensors and Actuators, 14 (1988) 19–25).

A certain degree of selectivity can be introduced by operating a $SnO_2$ sensor at different temperatures: Firth et al (Ann. Occup. Hyg., 18 (1975) 63–68) observed that a temperature of 300° C. resulted in response to the presence of CO but none to $CH_4$, while temperatures over 600° C. favoured $CH_4$ detection. Experiments have been performed by the applicants to see if this effect can be used by operating sensors in a temperature modulated mode. While good discrimination could be obtained for CO and $CH_4$ by operating the sensor at different temperatures, the presence of hydrogen ($H_2$) interfered. Not only did the sensors respond to $H_2$ at all temperatures but the response was erratic. There was also some evidence that gases were being adsorbed and then desorbed in subsequent tests (i.e. the sensors show a "memory effect").

By far the most popular method of achieving specificity is by the addition of catalysts or promoters. Researchers have reported that inclusions such as thorium dioxide confer CO selectivity, while the presence of silver improves $H_2$ response although not removing sensitivity to CO and $CH_4$. Such $H_2$ sensors incorporating silver have been reported by Yamazoe et al [(J.Chem. Sec. Japan them. Lett. (1982), 1899–1902) and (Sensors and Actuators, 4 (1983) 283–289)] in report showing apparently impressive sensitivity and selectivity for hydrogen. However the sensors described have several drawbacks.

Firstly they are not as sensitive and selective for hydrogen as appears at first sight from the graphs of results since, for example, $H_2$ concentration of 0.8% are being compared with CO concentrations of 0.02%, a forty-fold difference in concentration that dramatically effects the presentation of results.

Secondly peak hydrogen sensitivity is shifted to a temperature of ≈100° C. which is very low for such sensors which are usually held at in excess of 200° C. At such low temperatures as 100° C. problems can arise with condensation of volatiles on the sensor, even moisture being a problem. Additionally at such low temperatures the response time for the sensors would be very high. Response times are quoted in the above mentioned reports of 20 seconds to obtain a 90% response at 200° C.

Thirdly the response is not linear with concentration (see FIG. 3 of the Sensors and Actuators paper). and so complex calibration would be required.

The same authors have studied the effects of catalysts such as manganese, nickel, cobalt or copper on sensor response to various gases including CO, $CH_4$, $H_2$ and propane, while in most modern commercial sensors the presence of trace quantities (0.5–5% w/w) of palladium or platinum is an essential prerequisite.

There has also been described (Sensors and Actuators, 7 (1985) 89–96) the modification of tin oxide based gas sensors by inclusion of ~15% w/w bismuth oxide ($Bi_2O_3$) to give CO selectivity or 36% w/w aluminium silicate and 1.5% w/w palladium chloride ($PdCl_2$) for $CH_4$ selectivity. The CO selective sensor described was very sensitive to the amount of $Bi_2O_3$ present. Below 15% w/w the sensor was $CH_4$ sensitive; above 17% w/w the sensitivity to CO began to fall effectively disappearing at between 20–30% w/w.

U.K. Patent Application 2149123A describes sensors including, inter alia, $Bi_2Sn_2O_7$ and a gas sensitive material. Although, in discussing this material, the U.K. patent application describes gas sensitivity to $O_2$, $CH_4$, CO, $H_2$, $C_2H_4$, and $NH_3$ no indication is given as to relative sensitivities and selectivities for these gases.

SUMMARY OF THE INVENTION

Accordingly the present invention provides a method of measuring concentrations in gases comprising the use of a hydrogen sensor of the $SnO_2$ type comprising a layer of tin (IV) oxide ($Sno_2$) incorporating bismuth (III) oxide ($Bi_2O_3$) characterised in that the $Bi_2O_3$ is present in an amount less than 35% w/w based on the total amount of $SnO_2$ and $Bi_2O_3$ and sufficient that the sensor has hydrogen sensitivity and selectivity over the gases CO and $CH_4$.

More particularly, in accordance with the present invention there is provided a method of measuring hydrogen concentrations in gases comprising the use of a sensor of the $SnO_2$ type comprising a layer of tin (IV) oxide ($SnO_2$) incorporating bismuth (III) oxide ($Bi_2O_3$) wherein the $Bi_2O_3$ is present in an amount in excess of 17% by weight and less than 35% by weight based on the total amount of $SnO_2$ and $Bi_2O_3$ and sufficient that the sensor has hydrogen sensitivity and selectivity over the gases CO and $CH_4$.

In another aspect of the invention, the layer of tin (IV) oxide incorporating bismuth (III) oxide is deposited on a substrate from a slurry.

In accordance with another aspect of the invention, there is provided a hydrogen sensor for use in the above methods which contains a catalyst selected from one or more of the metals Ir, Pt, Ag, Ru, Au or Pd, and in which the amount of $Bi_2O_3$ is 22.5% by weight or above based on the total amount of $SnO_2$ and $Bi_2O_3$.

BRIEF DESCRIPTION OF THE INVENTION

Further features of the invention will be made evident in the claims and the following description with reference to the drawings in which:

Figure 4B:
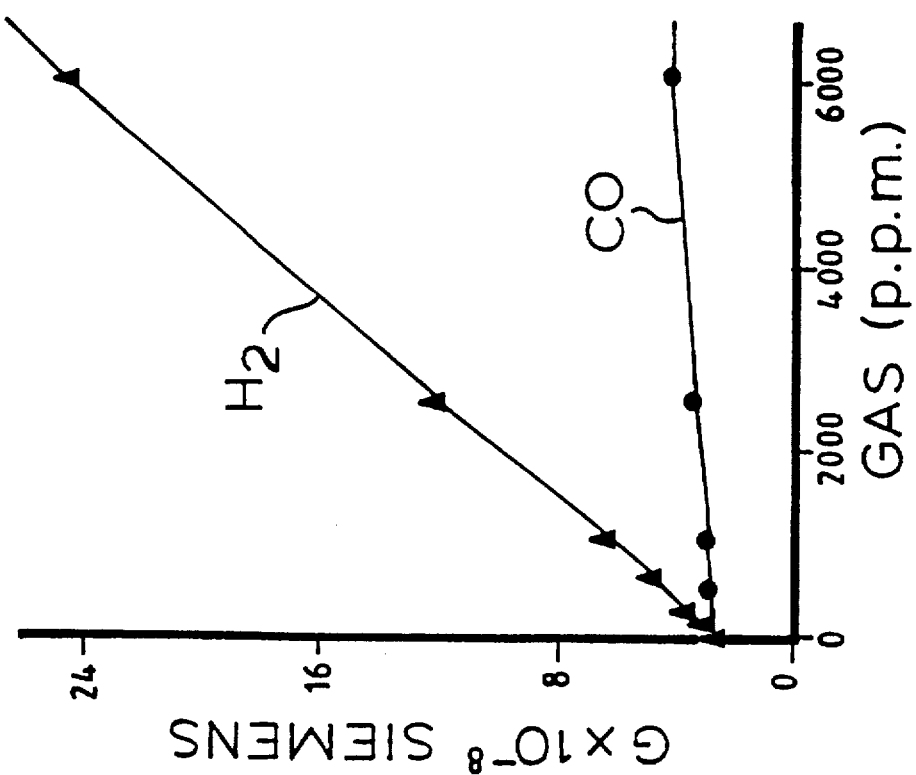
Figure 4A:
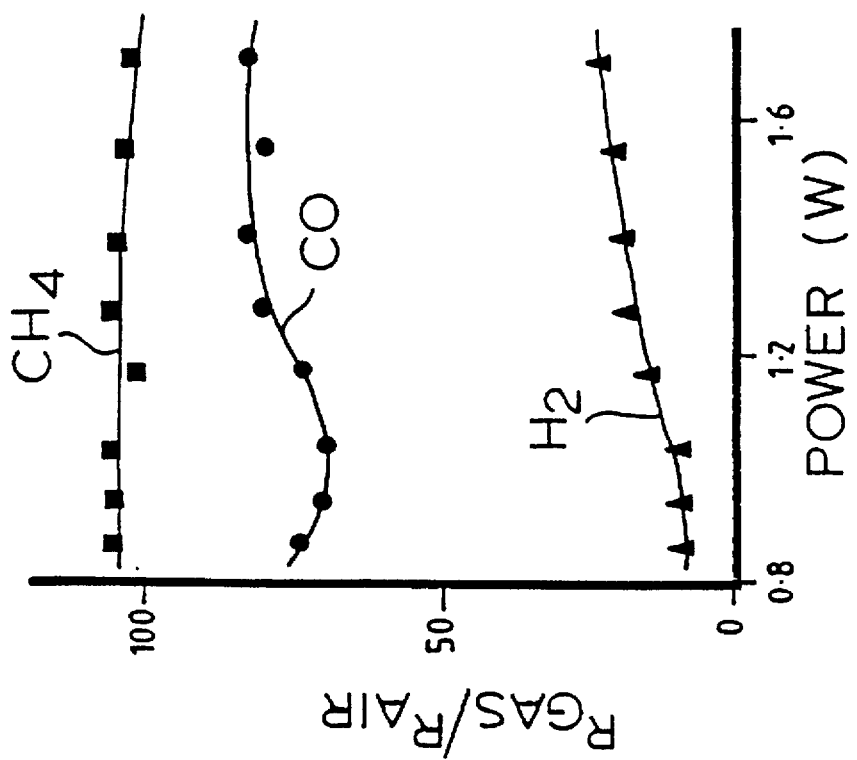
Figure 5:
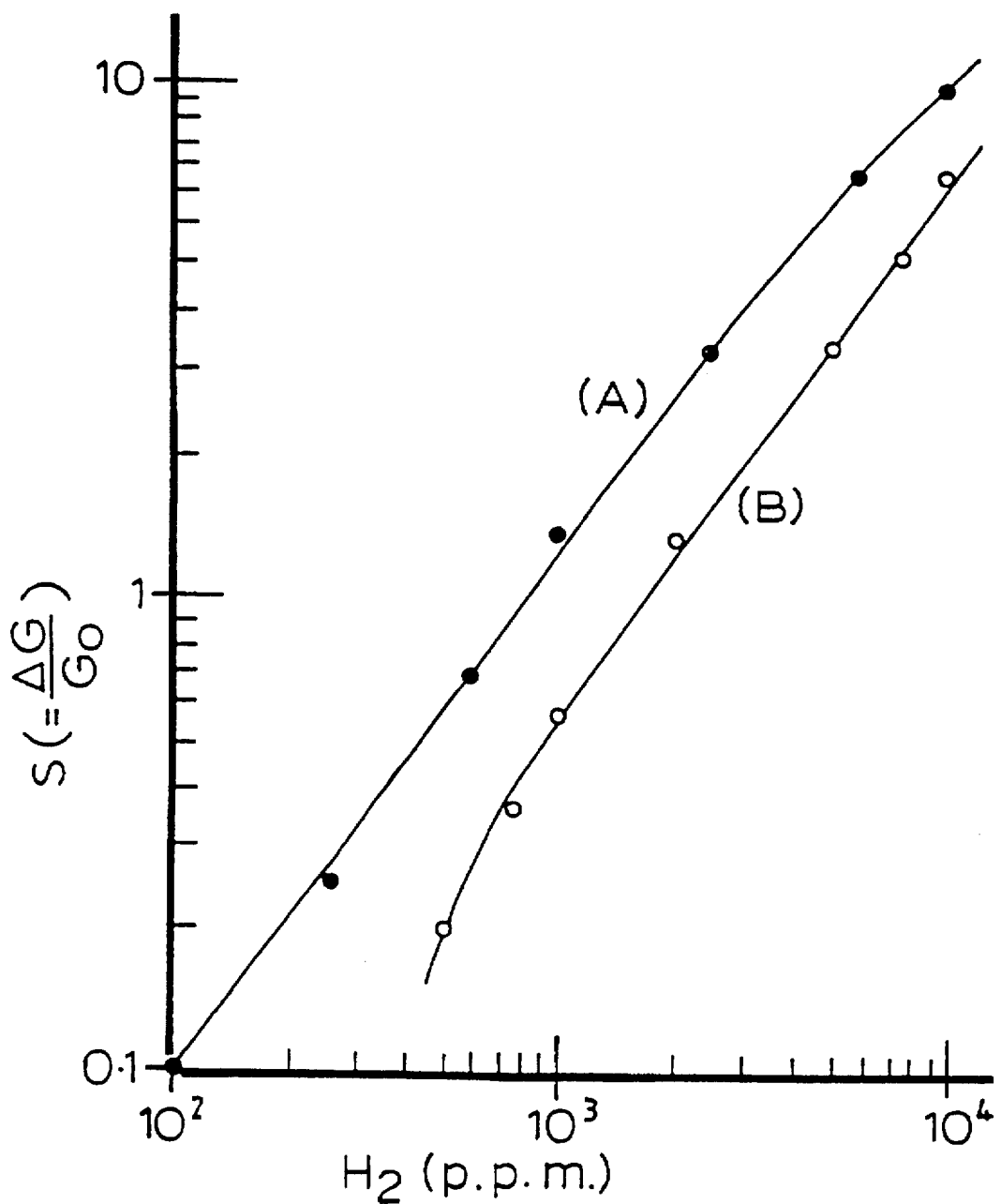

FIG. 3(a) and 3(b) shows the response characteristic of a particular preferred form of sensor:

FIG. 4(a) and 4(b) shows response characteristics of a further particular form of gas sensor;

FIG. 5 shows comparative results of the gas sensors referred to in relation to FIGS. 3(a) 4(b) and 4(a) and 4(b)

Figure 1:
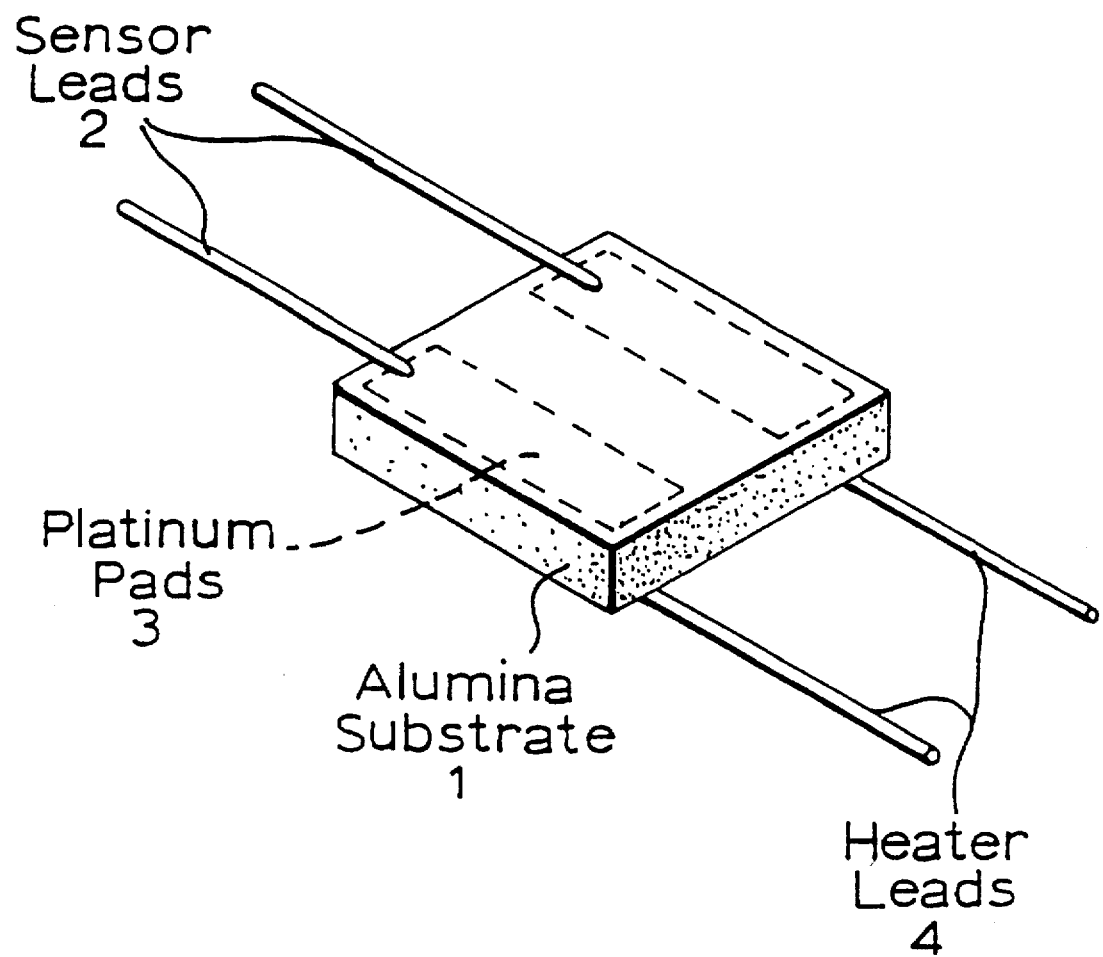
FIG. 1 is a schematic drawing of a gas sensor substrate.

FIG. 1 shows a $SnO_2$ gas sensor substrate comprising a plate 1 of ceramic material (e.g. alumina), sensor leads 2 connected with platinum contact pads 3 on the plate 1, and heater leads 4 connected with a platinum heater circuit (not shown) applied to the back face of the plate 1.

For experimental purposes hydrogen selective sensors were prepared from an aqueous slurry containing $SnO_2$, $Bi_2O_3$ (17%–30% w/w) and, in some cases, a metal catalyst (usually added in the form of a chloride salt, 1.5% w/w). A bead of this paste was then applied across the contact pads 3 of the alumina substrate as shown in FIG. 1 (alumina plate 1 supplied by Rosemount Engineering Ltd.), left to dry in air and then sintered at 1000° C. for 2 hours (using a furnace heating rate of 500° C./h). Some were sintered instead at 800° C. for comparative times.

In certain cases, sensors were fabricated from $SnO_2$/Pt powders prepared by deposition of a finely divided metal colloid. This procedure ensures that the sensor material is not contaminated by chloride ions which are released into the $SnO_2$ bead when the metal chloride additive is reduced to the metal itself.

The colloid was prepared by refluxing a solution containing 150mg of $H_2PtCl_6$ (Pt content=40% w/w), 150 cm$^3$ of a 1% w/v sodium citrate solution and 450 cm$^3$ of distilled water for a period of 5h. A very stable Pt/citrate colloid, black in colour, resulted.

The calculated concentration of metal in the colloidal system was 0.1 gdm$^{-3}$.

Deposition of the colloidal metal onto the $SnO_2$ surface was carried out via the following procedure. 1 gram of tin(IV) oxide powder was suspended in 100 cm$^3$ of the colloid and 11.6 g of NaCl was then added with continuous stirring. The resulting conditions of high ionic strength lead to destabilisation of the metal particles followed by precipitation (a process which appears to be complete within seconds). The solution was then left stirring for 1 h before filtering off the $SnO_2$/Pt powder and washing thoroughly with distilled water to remove Na$^+$, Cl$^-$ and citrate ions from the material.

A $SnO_2$+Ag powder was also prepared via the method outlined by Yamazoe et al, J. Chem. Soc. Japan Chem. Lett. 1982, 1899–1902 which consists of impregnating the stannic oxide with aqueous silver nitrate followed by evaporation to dryness and calcination at 600° C.

The $H_2$ sensing characteristics of these materials were then investigated after mixing into an aqueous slurry with $Bi_2O_3$ (25% w/w) and applying to the surface of an alumina substrate via the procedure described above.

Figure 2:
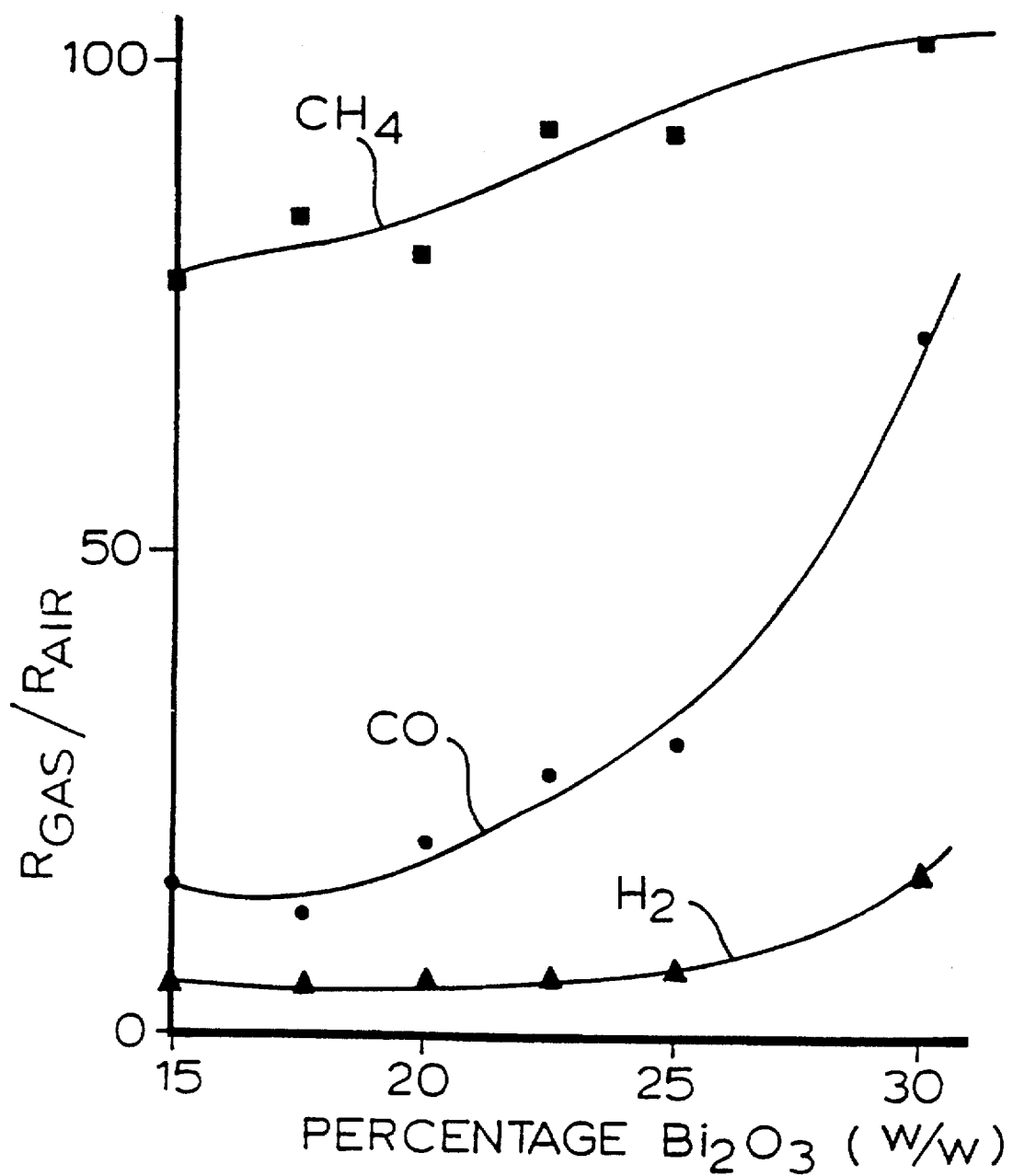
FIG. 2 illustrates sensor response as a function of increasing $Bi_2O_3$.

FIG. 2 illustrates the sensor response as a function of increasing $Bi_2O_3$ (15–30% w/w) composition in the presence of 1% v/v gas mixtures of $H_2$, CO or $CH_4$ in air. There appears to be a gradual decline in sensitivity to Co upon increasing $Bi_2O_3$ doping from 15% to 25% w/w whereas the loss of $H_2$ response under the same conditions is only very slight. At compositions of >30% w/w virtually all CO signal is lost while $H_2$ sensitivity remains reasonably substantial. However, a study of sensitivity to lower concentrations of $H_2$ and CO (100 and 1000 ppm) indicates that results gained using 1% v/v contaminant gas mixtures do not give a true overall picture. Data listed in Table 1 show a gradual decrease in $H_2$ sensitivity with increasing $Bi_2O_3$ content to both gas concentrations in an analogous manner to CO. Interestingly though, a comparison of the ratios of $H_2$ and CO sensitivities for a specified gas concentration and $Bi_2O_3$ composition (i.e. $S(H_2)S(CO)$) leads to the observation that $H_2$ response disappears at a slower rate than the CO signal upon increasing % $Bi_2O_3$. From the results listed in Table 1 it can be shown that $S(H_2)/S(CO)$ rises from 2 to 5 and from 1.8 to 9.5 for contaminant gas concentrations of 100 and 1000 ppm respectively when % $Bi_2O_3$ is increased in the range 15 to 30% w/w. Close scrutiny of FIG. 2 shows that an $SnO_2$-based sensor doped with 30% $Bi_2O_3$ (w/w) exhibits $H_2$ selectivity in the presence of CO and $CH_4$. However, results also indicate that such a sensor is not very responsive in the 0–1000 ppm $H_2$ concentration region although exhibiting relatively linear changes in conductance upon exposure to 0.1–1.0% v/v $H_2$/air mixtures.

Attempts to enhance the sensitivity of this $H_2$ sensor to low levels (100–1000 ppm) of contaminant gas were centred on reducing slightly the $Bi_2O_3$ content and including a metal catalyst to confer improved selectivity.

Table 2 shows the results obtained upon doping a $SnO_2$/$Bi_2O_3$ mixture of fixed proportion (23.5% w/w $Bi_2O_3$) with various metal catalysts (1.5% w/w added as chloride salt—final amount in sensor about 1% w/w). On inspection of the above table it seems that most of the metal additives improve sensor selectivity to $H_2$ compared with the undoped material, although this appears to be at the expense of some sensitivity. As a consequence the most promising sensors from those listed above (in terms of selectivity) are only suitable for detection of $H_2$ inclusions in the 500–10,000 ppm region e.g. sensors 3 and 7 (Ag and Ir) in Table 2. FIGS. 3(a) and 3(b) illustrate the response characteristics of a $SnO_2$/$Bi_2O_3$ (23.5% w/w) mixture doped with Iridium. Although the sensor exhibits a slight resistance drop in a 1% v/v air/CO mixture, FIG. 3(b) shows that in the 500–7000 ppm concentration range, the CO response is negligible. In contrast, $H_2$response is substantial and linear in this concentration region. Optimisation of the constituent proportions of a $SnO_2$/$Bi_2O_3$ mixture with added platinum yielded a further sensor exhibiting enhanced sensitivity (compared to the sensor described above) as well as $H_2$ selectivity. A "fine-tuned" $Bi_2O_3$ composition (an empirically determined compromise between selectivity and sensitivity), along with a platinum salt results in a $H_2$ selective $SnO_2$-based sensor whose response characteristics are shown in FIGS. 4(a) and 4(b). This comprised 25% w/w $Bi_2O_3$ (a compromise between selectivity and sensitivity) with 1.5% w/w $K_2PtCl_4$. The source of platinum did not appear to affect sensor response greatly, if anything the inclusion of other salts or finely divided colloidal platinum in place of the original salt served only to diminish sensitivity to a small extent. The linearity of $H_2$ response for both types of sensor described above is demonstrated clearly over a very wide concentration range (up to 2 orders of magnitude), by a plot of S versus $[H_2]$ using log–log axes (FIG. 5). Results obtained with $Bi_2O_3$ and Pt doped sensors are in conflict with Lee et al (Sensors and Actuators 12 (1987), 441–7) who observe enhanced CO sensitivity over $H_2$ when incorporating a platinum promoter in their thick film transducer. These workers report $S(=\Delta G/G_o)$ to be 1 and 0.35 for 200 ppm levels of CO and $H_2$ respectively at optimum operating temperature, while in our work S is 0.03 and 1.3 respectively for 1000 ppm of these gases.

A characteristic of the mixed $SnO_2/Bi_2O_3$ sensors is their high resistivities, and consequently they may be prepared using a substrate with an interdigitated contact array in order to reduce base resistances to easily measurable values. Alternatively, $Sb_2O_3$ (0–2% w/w) can be incorporated into a $H_2$sensor. This will reduce the resistivity by a factor of up to x 50 without sacrificing sensitivity or selectivity.

Another point worth noting is the difference between sensors sintered at 800° C. and 1000° C. If sensors are sintered at the higher of the two temperatures they tend to become "poisoned" (i.e. experience irreversible resistance drops) when exposed to $H_2$ and in some cases CO. This problem can be easily rectified by high power "cleaning", applying power to the heater leads at about 2 W for 1 minute and such a procedure should be borne in mind should this type of sensor be incorporated into a measuring device or alarm circuit.

One of the remarkable characteristics of this sensor is its linear response over a very wide (200–10,000 ppm) concentration range.

Additionally all of the $SnO_2/Bi_2O_3$ sensors studied had fast response times; most having a response time of less than 5 seconds to show a 100% response.

Although only single metal catalysts have been investigated it will be clear that mixed metal catalysts are within the scope of the invention.

TABLE 1

Sensitivity of $SnO_2$-based sensors doped with increasing amounts of $Bi_2O_3$.

| | CO | | $H_2$ | |
|---|---|---|---|---|
| % $Bi_2O_3$(w/w) | *S(100) | S(1000) | S(100) | S(1000) |
| 15 | 0.11 | 1.11 | 0.38 | 1.96 |
| 17.5 | 0.15 | 0.61 | 0.39 | 4.33 |
| 20 | 0.10 | 0.39 | 0.27 | 2.39 |
| 22.5 | 0.03 | 0.32 | 0.12 | 1.14 |
| 25 | 0.03 | 0.21 | 0.14 | 1.55 |
| 30 | <0.01 | 0.04 | 0.05 | 0.38 |

*s is defined as $\Delta G/G_o$ where $\Delta G$ is the change in conductance and $G_o$ is the conductance in air. The column headings S(100) or S(1000) specify whether sensitivity was measured in 100 ppm or 1000 ppm levels of contaminant gas. NB S(100) and S(1000) values for all sensors were <0.01 when exposed to $CH_4$.

TABLE 2

Response of various metal catalyst doped $H_2$ sensors to 1% v/v mixtures of CO, $H_2$ or $CH_4$ in air.

| Metal additive* | Optimum power (W) | $R_{CO}/R_{air}$ (%) | $R_{CH_4}/R_{air}$ (%) | $R_{H_2}/R_{air}$ (%) |
|---|---|---|---|---|
| 1 None | 0.93 | 29 | 93 | 7 |
| 2 Palladium | 0.96 | 44 | 107 | 14 |
| 3 Sliver | 0.90 | 66 | 106 | 8 |
| 4 Platinum | 0.93 | 45 | 98 | 6 |
| 5 Ruthenium | 0.90 | 94 | 106 | 30 |
| 6 Cold | 0.93 | 32 | 100 | 10 |
| 7 Iridium | 0.94 | 78 | 104 | 11 |

(b): Sensitivity of metal catalyst doped $H_2$ sensors to low contaminant gas concentrations (100 or 1000 ppm).

| | $H_2$ | | CO | |
|---|---|---|---|---|
| Metal additive | S(100) | S(1000) | S(100) | S(1000) |
| 1 None | 0.14 | 1.55 | 0.03 | 0.21 |
| 2 Palladium | 0.07 | 0.34 | 0 | 0.08 |
| 3 Silver | 0.16 | 0.53 | 0 | 0.01 |
| 4 Platinum | 0.12 | 1.32 | 0.07 | 0.35 |
| 5 Ruthenium | 0.08 | 0.58 | 0 | 0.04 |
| 6 Gold | 0.11 | 1.64 | 0.01 | 0.42 |
| 7 Iridium | <0.01 | 0.58 | 0 | 0.02 |

*sensor composition: $SnO_2$, $Bi_2O_3$, metal additive.
The sintering temperature in each case was 1000° C.

We claim:

1. A method of measuring hydrogen concentrations in gases comprising the use of a sensor of the $SnO_2$ type comprising a layer of tin (IV) oxide ($SnO_2$) incorporating bismuth (III) oxide ($Bi_2O_3$) wherein the $Bi_2O_3$ is present in an amount in excess of 17% by weight and less than 35% by weight based on the total amount of $SnO_2$ and $Bi_2O_3$ and sufficient that the sensor has hydrogen sensitivity and selectivity over the gases CO and $CH_4$.

2. A method as claimed in claim 1 in which the amount of $Bi_2O_3$ is in the range 20–30% by weight.

3. A method as claimed in claim 2 in which the amount of $Bi_2O_3$ is substantially about 23.5–25% by weight.

4. A hydrogen sensor for use in the method of claim 1 and which contains a catalyst selected from one or more of the metals Ir, Pt, Ag, Ru, Au or Pd, and in which the amount of $Bi_2O_3$ is 22.5% by weight or above based on the total amount of $SnO_2$ and $Bi_2O_3$.

5. A sensor as claimed in claim 4 in which the amount of $Bi_2O_3$ is 25% by weight or above based on the total amount of $SnO_2$ and $Bi_2O_3$.

6. A sensor as claimed in claim 5 comprising within the layer of tin (IV) oxide an addition of $Sb_2O_3$ in the amount of 0–2% by weight to reduce resistivity.

7. A method of measuring hydrogen concentrations in gases comprising the use of a sensor of the $SnO_2$ type comprising a layer of tin (IV) oxide ($SnO_2$) incorporating bismuth (III) oxide ($Bi_2O_3$) in which the $Bi_2O_3$ is present in an amount in excess of 17% by weight and less than 35% by weight based on the total amount of $SnO_2$ and $Bi_2O_3$ such that the sensor has hydrogen sensitivity and selectivity over the gases CO and $CH_4$ and in which the layer of tin (IV) oxide incorporating bismuth (III) oxide is deposited on a substrate from a slurry.

8. A method as claimed in claims 7 in which the amount of $Bi_2O_3$ is in the range 20–30% by weight.

9. A method as claimed in claim 8 in which the amount of $Bi_2O_3$ is substantially about 23.5–25% by weight.

10. A hydrogen sensor for use in the method of claim 7 and which contains a catalyst selected from one or more of the metals Ir, Pt, Ag, Ru, Au or Pd, and in which the amount of $Bi_2O_3$ is 22.5% by weight or above based on the total amount of $SnO_2$ and $Bi_2O_3$.

11. A sensor as claimed in claim 10 in which the amount of $Bi_2O_3$ is 25% by weight or above based on the total amount of $SnO_2$ and $Bi_2O_3$.

12. A sensor as claimed in claim 11 comprising within the layer of tin (IV) oxide an addition of $Sb_2O_3$ in the amount of 0–2% by weight to reduce resistivity.

* * * * *

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
( A ) LENGTH: 1607 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS 5,470,756

-continued ( B ) LOCATION: 356..1543

( x i ) SEQUENCE DESCRIPTION: SEQ ID NO:1:

```
GTCGACTCTA GAGTGTGTGT CAGCACTTGG CTGGGGACTT CTTGAACTTG CAGGGAGAAT        60

AACTTGCGCA CCCCACTTTG CGCCGGTGCC TTTGCCCCAG CGGAGCCTGC TTCGCCATCT       120

CCGAGCCCCA CCGCCCCTCC ACTCCTCGGC CTTGCCCGAC ACTGAGACGC TGTTCCCAGC       180

GTGAAAAGAG AGACTGCGCG GCCGGCACCC GGGAGAAGGA GGAGGCAAAG AAAAGGAACG       240

GACATTCGGT CCTTGCGCCA GGTCCTTTGA CCAGAGTTTT TCCATGTGGA CGCTCTTTCA       300

ATGGACGTGT CCCCGCGTGC TTCTTAGACG GACTGCGGTC TCCTAAAGGT CGACC ATG       358
                                                               Met
                                                                 1
```

| GTG | GCC | GGG | ACC | CGC | TGT | CTT | CTA | GCG | TTG | CTG | CTT | CCC | CAG | GTC | CTC | 406 |
|-----|-----|-----|-----|-----|-----|-----|-----|-----|-----|-----|-----|-----|-----|-----|-----|-----|
| Val | Ala | Gly | Thr | Arg | Cys | Leu | Leu | Ala | Leu | Leu | Leu | Pro | Gln | Val | Leu | |
|     |     |     | 5   |     |     |     |     | 10  |     |     |     |     | 15  |     |     |     |

| CTG | GGC | GGC | GCG | GCT | GGC | CTC | GTT | CCG | GAG | CTG | GGC | CGC | AGG | AAG | TTC | 454 |
|-----|-----|-----|-----|-----|-----|-----|-----|-----|-----|-----|-----|-----|-----|-----|-----|-----|
| Leu | Gly | Gly | Ala | Ala | Gly | Leu | Val | Pro | Glu | Leu | Gly | Arg | Arg | Lys | Phe | |
|     |     | 20  |     |     |     |     | 25  |     |     |     |     | 30  |     |     |     |     |

| GCG | GCG | GCG | TCG | TCG | GGC | CGC | CCC | TCA | TCC | CAG | CCC | TCT | GAC | GAG | GTC | 502 |
|-----|-----|-----|-----|-----|-----|-----|-----|-----|-----|-----|-----|-----|-----|-----|-----|-----|
| Ala | Ala | Ala | Ser | Ser | Gly | Arg | Pro | Ser | Ser | Gln | Pro | Ser | Asp | Glu | Val | |
|     | 35  |     |     |     |     | 40  |     |     |     |     | 45  |     |     |     |     |     |

| CTG | AGC | GAG | TTC | GAG | TTG | CGG | CTG | CTC | AGC | ATG | TTC | GGC | CTG | AAA | CAG | 550 |
|-----|-----|-----|-----|-----|-----|-----|-----|-----|-----|-----|-----|-----|-----|-----|-----|-----|
| Leu | Ser | Glu | Phe | Glu | Leu | Arg | Leu | Leu | Ser | Met | Phe | Gly | Leu | Lys | Gln | |
| 50  |     |     |     |     | 55  |     |     |     |     | 60  |     |     |     |     | 65  |     |

| AGA | CCC | ACC | CCC | AGC | AGG | GAC | GCC | GTG | GTG | CCC | CCC | TAC | ATG | CTA | GAC | 598 |
|-----|-----|-----|-----|-----|-----|-----|-----|-----|-----|-----|-----|-----|-----|-----|-----|-----|
| Arg | Pro | Thr | Pro | Ser | Arg | Asp | Ala | Val | Val | Pro | Pro | Tyr | Met | Leu | Asp | |
|     |     |     |     | 70  |     |     |     |     | 75  |     |     |     |     | 80  |     |     |

| CTG | TAT | CGC | AGG | CAC | TCA | GGT | CAG | CCG | GGC | TCA | CCC | GCC | CCA | GAC | CAC | 646 |
|-----|-----|-----|-----|-----|-----|-----|-----|-----|-----|-----|-----|-----|-----|-----|-----|-----|
| Leu | Tyr | Arg | Arg | His | Ser | Gly | Gln | Pro | Gly | Ser | Pro | Ala | Pro | Asp | His | |
|     |     |     | 85  |     |     |     |     | 90  |     |     |     |     | 95  |     |     |     |

| CGG | TTG | GAG | AGG | GCA | GCC | AGC | CGA | GCC | AAC | ACT | GTG | CGC | AGC | TTC | CAC | 694 |
|-----|-----|-----|-----|-----|-----|-----|-----|-----|-----|-----|-----|-----|-----|-----|-----|-----|
| Arg | Leu | Glu | Arg | Ala | Ala | Ser | Arg | Ala | Asn | Thr | Val | Arg | Ser | Phe | His | |
|     |     | 100 |     |     |     |     | 105 |     |     |     |     | 110 |     |     |     |     |

| CAT | GAA | GAA | TCT | TTG | GAA | GAA | CTA | CCA | GAA | ACG | AGT | GGG | AAA | ACA | ACC | 742 |
|-----|-----|-----|-----|-----|-----|-----|-----|-----|-----|-----|-----|-----|-----|-----|-----|-----|
| His | Glu | Glu | Ser | Leu | Glu | Glu | Leu | Pro | Glu | Thr | Ser | Gly | Lys | Thr | Thr | |
| 115 |     |     |     |     | 120 |     |     |     |     | 125 |     |     |     |     |     |     |

| CGG | AGA | TTC | TTC | TTT | AAT | TTA | AGT | TCT | ATC | CCC | ACG | GAG | GAG | TTT | ATC | 790 |
|-----|-----|-----|-----|-----|-----|-----|-----|-----|-----|-----|-----|-----|-----|-----|-----|-----|
| Arg | Arg | Phe | Phe | Phe | Asn | Leu | Ser | Ser | Ile | Pro | Thr | Glu | Glu | Phe | Ile | |
| 130 |     |     |     |     | 135 |     |     |     |     | 140 |     |     |     |     | 145 |     |

| ACC | TCA | GCA | GAG | CTT | CAG | GTT | TTC | CGA | GAA | CAG | ATG | CAA | GAT | GCT | TTA | 838 |
|-----|-----|-----|-----|-----|-----|-----|-----|-----|-----|-----|-----|-----|-----|-----|-----|-----|
| Thr | Ser | Ala | Glu | Leu | Gln | Val | Phe | Arg | Glu | Gln | Met | Gln | Asp | Ala | Leu | |
|     |     |     |     | 150 |     |     |     |     | 155 |     |     |     |     | 160 |     |     |

| GGA | AAC | AAT | AGC | AGT | TTC | CAT | CAC | CGA | ATT | AAT | ATT | TAT | GAA | ATC | ATA | 886 |
|-----|-----|-----|-----|-----|-----|-----|-----|-----|-----|-----|-----|-----|-----|-----|-----|-----|
| Gly | Asn | Asn | Ser | Ser | Phe | His | His | Arg | Ile | Asn | Ile | Tyr | Glu | Ile | Ile | |
|     |     |     | 165 |     |     |     |     | 170 |     |     |     |     | 175 |     |     |     |

| AAA | CCT | GCA | ACA | GCC | AAC | TCG | AAA | TTC | CCC | GTG | ACC | AGA | CTT | TTG | GAC | 934 |
|-----|-----|-----|-----|-----|-----|-----|-----|-----|-----|-----|-----|-----|-----|-----|-----|-----|
| Lys | Pro | Ala | Thr | Ala | Asn | Ser | Lys | Phe | Pro | Val | Thr | Arg | Leu | Leu | Asp | |
|     |     | 180 |     |     |     |     | 185 |     |     |     |     | 190 |     |     |     |     |

| ACC | AGG | TTG | GTG | AAT | CAG | AAT | GCA | AGC | AGG | TGG | GAA | ACT | TTT | GAT | GTC | 982 |
|-----|-----|-----|-----|-----|-----|-----|-----|-----|-----|-----|-----|-----|-----|-----|-----|-----|
| Thr | Arg | Leu | Val | Asn | Gln | Asn | Ala | Ser | Arg | Trp | Glu | Thr | Phe | Asp | Val | |
|     | 195 |     |     |     |     | 200 |     |     |     |     | 205 |     |     |     |     |     |

| ACC | CCC | GCT | GTG | ATG | CGG | TGG | ACT | GCA | CAG | GGA | CAC | GCC | AAC | CAT | GGA | 1030 |
|-----|-----|-----|-----|-----|-----|-----|-----|-----|-----|-----|-----|-----|-----|-----|-----|------|
| Thr | Pro | Ala | Val | Met | Arg | Trp | Thr | Ala | Gln | Gly | His | Ala | Asn | His | Gly | |
| 210 |     |     |     |     | 215 |     |     |     |     | 220 |     |     |     |     | 225 |     |

| TTC | GTG | GTG | GAA | GTG | GCC | CAC | TTG | GAG | GAG | AAA | CAA | GGT | GTC | TCC | AAG | 1078 |
|-----|-----|-----|-----|-----|-----|-----|-----|-----|-----|-----|-----|-----|-----|-----|-----|------|
| Phe | Val | Val | Glu | Val | Ala | His | Leu | Glu | Glu | Lys | Gln | Gly | Val | Ser | Lys | |
|     |     |     |     | 230 |     |     |     |     | 235 |     |     |     |     | 240 |     |     |

| AGA | CAT | GTT | AGG | ATA | AGC | AGG | TCT | TTG | CAC | CAA | GAT | GAA | CAC | AGC | TGG | 1126 |

| | | | | | | | | | | | | | | | |
|---|---|---|---|---|---|---|---|---|---|---|---|---|---|---|---|
|Arg|His|Val|Arg|Ile|Ser|Arg|Ser|Leu|His|Gln|Asp|Glu|His|Ser|Trp|
| | | |245| | | |250| | | | |255| | | |

| | | | | | | | | | | | | | | | | |
|---|---|---|---|---|---|---|---|---|---|---|---|---|---|---|---|---|
|TCA|CAG|ATA|AGG|CCA|TTG|CTA|GTA|ACT|TTT|GGC|CAT|GAT|GGA|AAA|GGG|1174|
|Ser|Gln|Ile|Arg|Pro|Leu|Leu|Val|Thr|Phe|Gly|His|Asp|Gly|Lys|Gly| |
| | |260| | | | |265| | | |270| | | | | |

| | | | | | | | | | | | | | | | | |
|---|---|---|---|---|---|---|---|---|---|---|---|---|---|---|---|---|
|CAT|CCT|CTC|CAC|AAA|AGA|GAA|AAA|CGT|CAA|GCC|AAA|CAC|AAA|CAG|CGG|1222|
|His|Pro|Leu|His|Lys|Arg|Glu|Lys|Arg|Gln|Ala|Lys|His|Lys|Gln|Arg| |
| |275| | | | |280| | | | |285| | | | | |

| | | | | | | | | | | | | | | | | |
|---|---|---|---|---|---|---|---|---|---|---|---|---|---|---|---|---|
|AAA|CGC|CTT|AAG|TCC|AGC|TGT|AAG|AGA|CAC|CCT|TTG|TAC|GTG|GAC|TTC|1270|
|Lys|Arg|Leu|Lys|Ser|Ser|Cys|Lys|Arg|His|Pro|Leu|Tyr|Val|Asp|Phe| |
|290| | | | |295| | | | |300| | | | |305| |

| | | | | | | | | | | | | | | | | |
|---|---|---|---|---|---|---|---|---|---|---|---|---|---|---|---|---|
|AGT|GAC|GTG|GGG|TGG|AAT|GAC|TGG|ATT|GTG|GCT|CCC|CCG|GGG|TAT|CAC|1318|
|Ser|Asp|Val|Gly|Trp|Asn|Asp|Trp|Ile|Val|Ala|Pro|Pro|Gly|Tyr|His| |
| | | | |310| | | |315| | | | |320| | | |

| | | | | | | | | | | | | | | | | |
|---|---|---|---|---|---|---|---|---|---|---|---|---|---|---|---|---|
|GCC|TTT|TAC|TGC|CAC|GGA|GAA|TGC|CCT|TTT|CCT|CTG|GCT|GAT|CAT|CTG|1366|
|Ala|Phe|Tyr|Cys|His|Gly|Glu|Cys|Pro|Phe|Pro|Leu|Ala|Asp|His|Leu| |
| | | |325| | | |330| | | | |335| | | | |

| | | | | | | | | | | | | | | | | |
|---|---|---|---|---|---|---|---|---|---|---|---|---|---|---|---|---|
|AAC|TCC|ACT|AAT|CAT|GCC|ATT|GTT|CAG|ACG|TTG|GTC|AAC|TCT|GTT|AAC|1414|
|Asn|Ser|Thr|Asn|His|Ala|Ile|Val|Gln|Thr|Leu|Val|Asn|Ser|Val|Asn| |
| | |340| | | | |345| | | | |350| | | | |

| | | | | | | | | | | | | | | | | |
|---|---|---|---|---|---|---|---|---|---|---|---|---|---|---|---|---|
|TCT|AAG|ATT|CCT|AAG|GCA|TGC|TGT|GTC|CCG|ACA|GAA|CTC|AGT|GCT|ATC|1462|
|Ser|Lys|Ile|Pro|Lys|Ala|Cys|Cys|Val|Pro|Thr|Glu|Leu|Ser|Ala|Ile| |
|355| | | | |360| | | | |365| | | | | | |

| | | | | | | | | | | | | | | | | |
|---|---|---|---|---|---|---|---|---|---|---|---|---|---|---|---|---|
|TCG|ATG|CTG|TAC|CTT|GAC|GAG|AAT|GAA|AAG|GTT|GTA|TTA|AAG|AAC|TAT|1510|
|Ser|Met|Leu|Tyr|Leu|Asp|Glu|Asn|Glu|Lys|Val|Val|Leu|Lys|Asn|Tyr| |
|370| | | | |375| | | | |380| | | | |385| |

| | | | | | | | | | | | |
|---|---|---|---|---|---|---|---|---|---|---|---|
|CAG|GAC|ATG|GTT|GTG|GAG|GGT|TGT|GGG|TGT|CGC|TAGTACAGCA AAATTAAATA|1563|
|Gln|Asp|Met|Val|Val|Glu|Gly|Cys|Gly|Cys|Arg| |
| | | |390| | | | |395| | | |

CATAAATATA TATATATATA TATATTTTAG AAAAAAGAAA AAAA    1607

( 2 ) INFORMATION FOR SEQ ID NO:2:

( i ) SEQUENCE CHARACTERISTICS:
        ( A ) LENGTH: 396 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Val|Ala|Gly|Thr|Arg|Cys|Leu|Leu|Ala|Leu|Leu|Leu|Pro|Gln|Val|
|1| | | |5| | | | |10| | | | |15|

| | | | | | | | | | | | | | | |
|---|---|---|---|---|---|---|---|---|---|---|---|---|---|---|
|Leu|Leu|Gly|Gly|Ala|Ala|Gly|Leu|Val|Pro|Glu|Leu|Gly|Arg|Arg|Lys|
| | | |20| | | | |25| | | | |30| |

| | | | | | | | | | | | | | | |
|---|---|---|---|---|---|---|---|---|---|---|---|---|---|---|
|Phe|Ala|Ala|Ala|Ser|Ser|Gly|Arg|Pro|Ser|Ser|Gln|Pro|Ser|Asp|Glu|
| | |35| | | | |40| | | | |45| | |

| | | | | | | | | | | | | | | |
|---|---|---|---|---|---|---|---|---|---|---|---|---|---|---|
|Val|Leu|Ser|Glu|Phe|Glu|Leu|Arg|Leu|Leu|Ser|Met|Phe|Gly|Leu|Lys|
| |50| | | | |55| | | | |60| | | |

| | | | | | | | | | | | | | | |
|---|---|---|---|---|---|---|---|---|---|---|---|---|---|---|
|Gln|Arg|Pro|Thr|Pro|Ser|Arg|Asp|Ala|Val|Val|Pro|Pro|Tyr|Met|Leu|
|65| | | | |70| | | | |75| | | | |80|

| | | | | | | | | | | | | | | |
|---|---|---|---|---|---|---|---|---|---|---|---|---|---|---|
|Asp|Leu|Tyr|Arg|Arg|His|Ser|Gly|Gln|Pro|Gly|Ser|Pro|Ala|Pro|Asp|
| | | |85| | | | |90| | | | |95| |

| | | | | | | | | | | | | | | |
|---|---|---|---|---|---|---|---|---|---|---|---|---|---|---|
|His|Arg|Leu|Glu|Arg|Ala|Ala|Ser|Arg|Ala|Asn|Thr|Val|Arg|Ser|Phe|
| | |100| | | | |105| | | | |110| | |

| | | | | | | | | | | | | | | |
|---|---|---|---|---|---|---|---|---|---|---|---|---|---|---|
|His|His|Glu|Glu|Ser|Leu|Glu|Glu|Leu|Pro|Glu|Thr|Ser|Gly|Lys|Thr|
| |115| | | | |120| | | | |125| | | |

| | | | | | | | | | | | | |
|---|---|---|---|---|---|---|---|---|---|---|---|---|
|Thr|Arg|Arg|Phe|Phe|Phe|Asn|Leu|Ser|Ser|Ile|Pro|Thr|Glu|Glu|Phe|
|130| | | | |135| | | | |140| | | | | |

| | | | | | | | | | | | | | | | |
|---|---|---|---|---|---|---|---|---|---|---|---|---|---|---|---|
| Ile | Thr | Ser | Ala | Glu | Leu | Gln | Val | Phe | Arg | Glu | Gln | Met | Gln | Asp | Ala |
| 145 | | | | 150 | | | | | 155 | | | | | | 160 |
| Leu | Gly | Asn | Asn | Ser | Ser | Phe | His | His | Arg | Ile | Asn | Ile | Tyr | Glu | Ile |
| | | | | 165 | | | | | 170 | | | | | 175 | |
| Ile | Lys | Pro | Ala | Thr | Ala | Asn | Ser | Lys | Phe | Pro | Val | Thr | Arg | Leu | Leu |
| | | | 180 | | | | | 185 | | | | | 190 | | |
| Asp | Thr | Arg | Leu | Val | Asn | Gln | Asn | Ala | Ser | Arg | Trp | Glu | Thr | Phe | Asp |
| | | 195 | | | | | 200 | | | | | 205 | | | |
| Val | Thr | Pro | Ala | Val | Met | Arg | Trp | Thr | Ala | Gln | Gly | His | Ala | Asn | His |
| | 210 | | | | | 215 | | | | | 220 | | | | |
| Gly | Phe | Val | Val | Glu | Val | Ala | His | Leu | Glu | Glu | Lys | Gln | Gly | Val | Ser |
| 225 | | | | | 230 | | | | | 235 | | | | | 240 |
| Lys | Arg | His | Val | Arg | Ile | Ser | Arg | Ser | Leu | His | Gln | Asp | Glu | His | Ser |
| | | | | 245 | | | | | 250 | | | | | 255 | |
| Trp | Ser | Gln | Ile | Arg | Pro | Leu | Leu | Val | Thr | Phe | Gly | His | Asp | Gly | Lys |
| | | | 260 | | | | | 265 | | | | | 270 | | |
| Gly | His | Pro | Leu | His | Lys | Arg | Glu | Lys | Arg | Gln | Ala | Lys | His | Lys | Gln |
| | | 275 | | | | | 280 | | | | | 285 | | | |
| Arg | Lys | Arg | Leu | Lys | Ser | Ser | Cys | Lys | Arg | His | Pro | Leu | Tyr | Val | Asp |
| | 290 | | | | | 295 | | | | | 300 | | | | |
| Phe | Ser | Asp | Val | Gly | Trp | Asn | Asp | Trp | Ile | Val | Ala | Pro | Pro | Gly | Tyr |
| 305 | | | | | 310 | | | | | 315 | | | | | 320 |
| His | Ala | Phe | Tyr | Cys | His | Gly | Glu | Cys | Pro | Phe | Pro | Leu | Ala | Asp | His |
| | | | | 325 | | | | | 330 | | | | | 335 | |
| Leu | Asn | Ser | Thr | Asn | His | Ala | Ile | Val | Gln | Thr | Leu | Val | Asn | Ser | Val |
| | | | 340 | | | | | 345 | | | | | 350 | | |
| Asn | Ser | Lys | Ile | Pro | Lys | Ala | Cys | Cys | Val | Pro | Thr | Glu | Leu | Ser | Ala |
| | | 355 | | | | | 360 | | | | | 365 | | | |
| Ile | Ser | Met | Leu | Tyr | Leu | Asp | Glu | Asn | Glu | Lys | Val | Val | Leu | Lys | Asn |
| | 370 | | | | | 375 | | | | | 380 | | | | |
| Tyr | Gln | Asp | Met | Val | Val | Glu | Gly | Cys | Gly | Cys | Arg | | | | |
| 385 | | | | | 390 | | | | | 395 | | | | | |

( 2 ) INFORMATION FOR SEQ ID NO:3:

( i ) SEQUENCE CHARACTERISTICS:
        ( A ) LENGTH: 1954 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 403..1626

( x i ) SEQUENCE DESCRIPTION: SEQ ID NO:3:

| | | | | | | |
|---|---|---|---|---|---|---|
| CTCTAGAGGG | CAGAGGAGGA | GGGAGGGAGG | GAAGGAGCGC | GGAGCCCGGC | CCGGAAGCTA | 60 |
| GGTGAGTGTG | GCATCCGAGC | TGAGGGACGC | GAGCCTGAGA | CGCCGCTGCT | GCTCCGGCTG | 120 |
| AGTATCTAGC | TTGTCTCCCC | GATGGGATTC | CCGTCCAAGC | TATCTCGAGC | CTGCAGCGCC | 180 |
| ACAGTCCCCG | GCCCTCGCCC | AGGTTCACTG | CAACCGTTCA | GAGGTCCCCA | GGAGCTGCTG | 240 |
| CTGGCGAGCC | CGCTACTGCA | GGGACCTATG | GAGCCATTCC | GTAGTGCCAT | CCCGAGCAAC | 300 |
| GCACTGCTGC | AGCTTCCCTG | AGCCTTTCCA | GCAAGTTTGT | TCAAGATTGG | CTGTCAAGAA | 360 |
| TCATGGACTG | TTATTATATG | CCTTGTTTTC | TGTCAAGACA | CC ATG ATT CCT GGT | | 414 |

|     |     |     |     |     |     |     |     |     |     |     | Met | Ile | Pro | Gly |      |
|-----|-----|-----|-----|-----|-----|-----|-----|-----|-----|-----|-----|-----|-----|-----|------|
|     |     |     |     |     |     |     |     |     |     |     |     |  1  |     |     |      |

| AAC | CGA | ATG | CTG | ATG | GTC | GTT | TTA | TTA | TGC | CAA | GTC | CTG | CTA | GGA | GGC | 462 |
|-----|-----|-----|-----|-----|-----|-----|-----|-----|-----|-----|-----|-----|-----|-----|-----|-----|
| Asn | Arg | Met | Leu | Met | Val | Val | Leu | Leu | Cys | Gln | Val | Leu | Leu | Gly | Gly |     |
| 5   |     |     |     | 10  |     |     |     |     | 15  |     |     |     |     | 20  |     |     |

| GCG | AGC | CAT | GCT | AGT | TTG | ATA | CCT | GAG | ACG | GGG | AAG | AAA | AAA | GTC | GCC | 510 |
| Ala | Ser | His | Ala | Ser | Leu | Ile | Pro | Glu | Thr | Gly | Lys | Lys | Lys | Val | Ala |     |
|     |     |     |     | 25  |     |     |     |     | 30  |     |     |     |     | 35  |     |     |

| GAG | ATT | CAG | GGC | CAC | GCG | GGA | GGA | CGC | CGC | TCA | GGG | CAG | AGC | CAT | GAG | 558 |
| Glu | Ile | Gln | Gly | His | Ala | Gly | Gly | Arg | Arg | Ser | Gly | Gln | Ser | His | Glu |     |
|     |     |     |     | 40  |     |     |     |     | 45  |     |     |     |     | 50  |     |     |

| CTC | CTG | CGG | GAC | TTC | GAG | GCG | ACA | CTT | CTG | CAG | ATG | TTT | GGG | CTG | CGC | 606 |
| Leu | Leu | Arg | Asp | Phe | Glu | Ala | Thr | Leu | Leu | Gln | Met | Phe | Gly | Leu | Arg |     |
|     |     | 55  |     |     |     |     | 60  |     |     |     |     | 65  |     |     |     |     |

| CGC | CGC | CCG | CAG | CCT | AGC | AAG | AGT | GCC | GTC | ATT | CCG | GAC | TAC | ATG | CGG | 654 |
| Arg | Arg | Pro | Gln | Pro | Ser | Lys | Ser | Ala | Val | Ile | Pro | Asp | Tyr | Met | Arg |     |
|     |     | 70  |     |     |     |     | 75  |     |     |     |     | 80  |     |     |     |     |

| GAT | CTT | TAC | CGG | CTT | CAG | TCT | GGG | GAG | GAG | GAG | GAA | GAG | CAG | ATC | CAC | 702 |
| Asp | Leu | Tyr | Arg | Leu | Gln | Ser | Gly | Glu | Glu | Glu | Glu | Glu | Gln | Ile | His |     |
| 85  |     |     |     |     | 90  |     |     |     |     | 95  |     |     |     |     | 100 |     |

| AGC | ACT | GGT | CTT | GAG | TAT | CCT | GAG | CGC | CCG | GCC | AGC | CGG | GCC | AAC | ACC | 750 |
| Ser | Thr | Gly | Leu | Glu | Tyr | Pro | Glu | Arg | Pro | Ala | Ser | Arg | Ala | Asn | Thr |     |
|     |     |     |     | 105 |     |     |     |     | 110 |     |     |     |     | 115 |     |     |

| GTG | AGG | AGC | TTC | CAC | CAC | GAA | GAA | CAT | CTG | GAG | AAC | ATC | CCA | GGG | ACC | 798 |
| Val | Arg | Ser | Phe | His | His | Glu | Glu | His | Leu | Glu | Asn | Ile | Pro | Gly | Thr |     |
|     |     |     |     | 120 |     |     |     |     | 125 |     |     |     |     | 130 |     |     |

| AGT | GAA | AAC | TCT | GCT | TTT | CGT | TTC | CTC | TTT | AAC | CTC | AGC | AGC | ATC | CCT | 846 |
| Ser | Glu | Asn | Ser | Ala | Phe | Arg | Phe | Leu | Phe | Asn | Leu | Ser | Ser | Ile | Pro |     |
|     |     |     |     | 135 |     |     |     |     | 140 |     |     |     |     | 145 |     |     |

| GAG | AAC | GAG | GTG | ATC | TCC | TCT | GCA | GAG | CTT | CGG | CTC | TTC | CGG | GAG | CAG | 894 |
| Glu | Asn | Glu | Val | Ile | Ser | Ser | Ala | Glu | Leu | Arg | Leu | Phe | Arg | Glu | Gln |     |
|     |     | 150 |     |     |     |     | 155 |     |     |     |     | 160 |     |     |     |     |

| GTG | GAC | CAG | GGC | CCT | GAT | TGG | GAA | AGG | GGC | TTC | CAC | CGT | ATA | AAC | ATT | 942 |
| Val | Asp | Gln | Gly | Pro | Asp | Trp | Glu | Arg | Gly | Phe | His | Arg | Ile | Asn | Ile |     |
| 165 |     |     |     |     | 170 |     |     |     |     | 175 |     |     |     |     | 180 |     |

| TAT | GAG | GTT | ATG | AAG | CCC | CCA | GCA | GAA | GTG | GTG | CCT | GGG | CAC | CTC | ATC | 990 |
| Tyr | Glu | Val | Met | Lys | Pro | Pro | Ala | Glu | Val | Val | Pro | Gly | His | Leu | Ile |     |
|     |     |     |     | 185 |     |     |     |     | 190 |     |     |     |     | 195 |     |     |

| ACA | CGA | CTA | CTG | GAC | ACG | AGA | CTG | GTC | CAC | CAC | AAT | GTG | ACA | CGG | TGG | 1038 |
| Thr | Arg | Leu | Leu | Asp | Thr | Arg | Leu | Val | His | His | Asn | Val | Thr | Arg | Trp |      |
|     |     |     |     | 200 |     |     |     |     | 205 |     |     |     |     | 210 |     |      |

| GAA | ACT | TTT | GAT | GTG | AGC | CCT | GCG | GTC | CTT | CGC | TGG | ACC | CGG | GAG | AAG | 1086 |
| Glu | Thr | Phe | Asp | Val | Ser | Pro | Ala | Val | Leu | Arg | Trp | Thr | Arg | Glu | Lys |      |
|     |     |     |     | 215 |     |     |     |     | 220 |     |     |     |     | 225 |     |      |

| CAG | CCA | AAC | TAT | GGG | CTA | GCC | ATT | GAG | GTG | ACT | CAC | CTC | CAT | CAG | ACT | 1134 |
| Gln | Pro | Asn | Tyr | Gly | Leu | Ala | Ile | Glu | Val | Thr | His | Leu | His | Gln | Thr |      |
|     |     | 230 |     |     |     |     | 235 |     |     |     |     | 240 |     |     |     |      |

| CGG | ACC | CAC | CAG | GGC | CAG | CAT | GTC | AGG | ATT | AGC | CGA | TCG | TTA | CCT | CAA | 1182 |
| Arg | Thr | His | Gln | Gly | Gln | His | Val | Arg | Ile | Ser | Arg | Ser | Leu | Pro | Gln |      |
| 245 |     |     |     |     | 250 |     |     |     |     | 255 |     |     |     |     | 260 |      |

| GGG | AGT | GGG | AAT | TGG | GCC | CAG | CTC | CGG | CCC | CTC | CTG | GTC | ACC | TTT | GGC | 1230 |
| Gly | Ser | Gly | Asn | Trp | Ala | Gln | Leu | Arg | Pro | Leu | Leu | Val | Thr | Phe | Gly |      |
|     |     |     |     | 265 |     |     |     |     | 270 |     |     |     |     | 275 |     |      |

| CAT | GAT | GGC | CGG | GGC | CAT | GCC | TTG | ACC | CGA | CGC | CGG | AGG | GCC | AAG | CGT | 1278 |
| His | Asp | Gly | Arg | Gly | His | Ala | Leu | Thr | Arg | Arg | Arg | Arg | Ala | Lys | Arg |      |
|     |     |     |     | 280 |     |     |     |     | 285 |     |     |     |     | 290 |     |      |

| AGC | CCT | AAG | CAT | CAC | TCA | CAG | CGG | GCC | AGG | AAG | AAG | AAT | AAG | AAC | TGC | 1326 |
| Ser | Pro | Lys | His | His | Ser | Gln | Arg | Ala | Arg | Lys | Lys | Asn | Lys | Asn | Cys |      |
|     |     | 295 |     |     |     |     | 300 |     |     |     |     | 305 |     |     |     |      |

```
CGG CGC CAC TCG CTC TAT GTG GAC TTC AGC GAT GTG GGC TGG AAT GAC          1374
Arg Arg His Ser Leu Tyr Val Asp Phe Ser Asp Val Gly Trp Asn Asp
    310             315                 320

TGG ATT GTG GCC CCA CCA GGC TAC CAG GCC TTC TAC TGC CAT GGG GAC          1422
Trp Ile Val Ala Pro Pro Gly Tyr Gln Ala Phe Tyr Cys His Gly Asp
325             330                 335                 340

TGC CCC TTT CCA CTG GCT GAC CAC CTC AAC TCA ACC AAC CAT GCC ATT          1470
Cys Pro Phe Pro Leu Ala Asp His Leu Asn Ser Thr Asn His Ala Ile
                345                 350                 355

GTG CAG ACC CTG GTC AAT TCT GTC AAT TCC AGT ATC CCC AAA GCC TGT          1518
Val Gln Thr Leu Val Asn Ser Val Asn Ser Ser Ile Pro Lys Ala Cys
            360                 365                 370

TGT GTG CCC ACT GAA CTG AGT GCC ATC TCC ATG CTG TAC CTG GAT GAG          1566
Cys Val Pro Thr Glu Leu Ser Ala Ile Ser Met Leu Tyr Leu Asp Glu
        375                 380                 385

TAT GAT AAG GTG GTA CTG AAA AAT TAT CAG GAG ATG GTA GTA GAG GGA          1614
Tyr Asp Lys Val Val Leu Lys Asn Tyr Gln Glu Met Val Val Glu Gly
    390             395                 400

TGT GGG TGC CGC TGAGATCAGG CAGTCCTTGA GGATAGACAG ATATACACAC              1666
Cys Gly Cys Arg
405

CACACACACA CACCACATAC ACCACACACA CACGTTCCCA TCCACTCACC CACACACTAC       1726

ACAGACTGCT TCCTTATAGC TGGACTTTTA TTTAAAAAAA AAAAAAAAAA AATGGAAAAA       1786

ATCCCTAAAC ATTCACCTTG ACCTTATTTA TGACTTTACG TGCAAATGTT TTGACCATAT       1846

TGATCATATA TTTTGACAAA ATATATTTAT AACTACGTAT TAAAAGAAAA AAATAAAATG       1906

AGTCATTATT TTAAAAAAAA AAAAAAAACT CTAGAGTCGA CGGAATTC                    1954
```

( 2 ) INFORMATION FOR SEQ ID NO:4:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
130                 135                 140

Ser Ser Ile Pro Glu Asn Glu Val Ile Ser Ser Ala Glu Leu Arg Leu
145                 150                 155                 160
```

| | | | | | | | | | | | | | |
|---|---|---|---|---|---|---|---|---|---|---|---|---|---|
| Phe | Arg | Glu | Gln | Val | Asp | Gln | Gly | Pro | Asp | Trp | Glu | Arg | Gly | Phe | His |
| | | | | 165 | | | | 170 | | | | | 175 |
| Arg | Ile | Asn | Ile | Tyr | Glu | Val | Met | Lys | Pro | Pro | Ala | Glu | Val | Val | Pro |
| | | | 180 | | | | | 185 | | | | | 190 |
| Gly | His | Leu | Ile | Thr | Arg | Leu | Leu | Asp | Thr | Arg | Leu | Val | His | His | Asn |
| | | 195 | | | | | 200 | | | | | 205 |
| Val | Thr | Arg | Trp | Glu | Thr | Phe | Asp | Val | Ser | Pro | Ala | Val | Leu | Arg | Trp |
| | 210 | | | | | 215 | | | | | 220 |
| Thr | Arg | Glu | Lys | Gln | Pro | Asn | Tyr | Gly | Leu | Ala | Ile | Glu | Val | Thr | His |
| 225 | | | | | 230 | | | | | 235 | | | | | 240 |
| Leu | His | Gln | Thr | Arg | Thr | His | Gln | Gly | Gln | His | Val | Arg | Ile | Ser | Arg |
| | | | | 245 | | | | | 250 | | | | | 255 |
| Ser | Leu | Pro | Gln | Gly | Ser | Gly | Asn | Trp | Ala | Gln | Leu | Arg | Pro | Leu | Leu |
| | | | 260 | | | | | 265 | | | | | 270 |
| Val | Thr | Phe | Gly | His | Asp | Gly | Arg | Gly | His | Ala | Leu | Thr | Arg | Arg | Arg |
| | | 275 | | | | | 280 | | | | | 285 |
| Arg | Ala | Lys | Arg | Ser | Pro | Lys | His | His | Ser | Gln | Arg | Ala | Arg | Lys | Lys |
| | 290 | | | | | 295 | | | | | 300 |
| Asn | Lys | Asn | Cys | Arg | Arg | His | Ser | Leu | Tyr | Val | Asp | Phe | Ser | Asp | Val |
| 305 | | | | | 310 | | | | | 315 | | | | | 320 |
| Gly | Trp | Asn | Asp | Trp | Ile | Val | Ala | Pro | Pro | Gly | Tyr | Gln | Ala | Phe | Tyr |
| | | | | 325 | | | | | 330 | | | | | 335 |
| Cys | His | Gly | Asp | Cys | Pro | Phe | Pro | Leu | Ala | Asp | His | Leu | Asn | Ser | Thr |
| | | | 340 | | | | | 345 | | | | | 350 |
| Asn | His | Ala | Ile | Val | Gln | Thr | Leu | Val | Asn | Ser | Val | Asn | Ser | Ser | Ile |
| | | 355 | | | | | 360 | | | | | 365 |
| Pro | Lys | Ala | Cys | Cys | Val | Pro | Thr | Glu | Leu | Ser | Ala | Ile | Ser | Met | Leu |
| | 370 | | | | | 375 | | | | | 380 |
| Tyr | Leu | Asp | Glu | Tyr | Asp | Lys | Val | Val | Leu | Lys | Asn | Tyr | Gln | Glu | Met |
| 385 | | | | | 390 | | | | | 395 | | | | | 400 |
| Val | Val | Glu | Gly | Cys | Gly | Cys | Arg |
| | | | | 405 |

( 2 ) INFORMATION FOR SEQ ID NO:5:

( i ) SEQUENCE CHARACTERISTICS:
        ( A ) LENGTH: 1448 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 97..1389

( x i ) SEQUENCE DESCRIPTION: SEQ ID NO:5:

```
GTGACCGAGC  GGCGCGGACG  GCCGCCTGCC  CCCTCTGCCA  CCTGGGGCGG  TGCGGGCCCG          60

GAGCCCGGAG  CCCGGGTAGC  GCGTAGAGCC  GGCGCG ATG  CAC  GTG  CGC  TCA  CTG        114
                                           Met  His  Val  Arg  Ser  Leu
                                             1                       5

CGA  GCT  GCG  GCG  CCG  CAC  AGC  TTC  GTG  GCG  CTC  TGG  GCA  CCC  CTG  TTC  162
Arg  Ala  Ala  Ala  Pro  His  Ser  Phe  Val  Ala  Leu  Trp  Ala  Pro  Leu  Phe
               10                    15                        20

CTG  CTG  CGC  TCC  GCC  CTG  GCC  GAC  TTC  AGC  CTG  GAC  AAC  GAG  GTG  CAC  210
Leu  Leu  Arg  Ser  Ala  Leu  Ala  Asp  Phe  Ser  Leu  Asp  Asn  Glu  Val  His
          25                    30                        35
```

-continued

```
TCG  AGC  TTC  ATC  CAC  CGG  CGC  CTC  CGC  AGC  CAG  GAG  CGG  CGG  GAG  ATG    258
Ser  Ser  Phe  Ile  His  Arg  Arg  Leu  Arg  Ser  Gln  Glu  Arg  Arg  Glu  Met
     40                       45                      50

CAG  CGC  GAG  ATC  CTC  TCC  ATT  TTG  GGC  TTG  CCC  CAC  CGC  CCG  CGC  CCG    306
Gln  Arg  Glu  Ile  Leu  Ser  Ile  Leu  Gly  Leu  Pro  His  Arg  Pro  Arg  Pro
55                       60                      65                          70

CAC  CTC  CAG  GGC  AAG  CAC  AAC  TCG  GCA  CCC  ATG  TTC  ATG  CTG  GAC  CTG    354
His  Leu  Gln  Gly  Lys  His  Asn  Ser  Ala  Pro  Met  Phe  Met  Leu  Asp  Leu
               75                       80                      85

TAC  AAC  GCC  ATG  GCG  GTG  GAG  GAG  GGC  GGC  GGG  CCC  GGC  GGC  CAG  GGC    402
Tyr  Asn  Ala  Met  Ala  Val  Glu  Glu  Gly  Gly  Gly  Pro  Gly  Gly  Gln  Gly
                    90                      95                     100

TTC  TCC  TAC  CCC  TAC  AAG  GCC  GTC  TTC  AGT  ACC  CAG  GGC  CCC  CCT  CTG    450
Phe  Ser  Tyr  Pro  Tyr  Lys  Ala  Val  Phe  Ser  Thr  Gln  Gly  Pro  Pro  Leu
               105                      110                     115

GCC  AGC  CTG  CAA  GAT  AGC  CAT  TTC  CTC  ACC  GAC  GCC  GAC  ATG  GTC  ATG    498
Ala  Ser  Leu  Gln  Asp  Ser  His  Phe  Leu  Thr  Asp  Ala  Asp  Met  Val  Met
     120                      125                     130

AGC  TTC  GTC  AAC  CTC  GTG  GAA  CAT  GAC  AAG  GAA  TTC  TTC  CAC  CCA  CGC    546
Ser  Phe  Val  Asn  Leu  Val  Glu  His  Asp  Lys  Glu  Phe  Phe  His  Pro  Arg
135                      140                     145                         150

TAC  CAC  CAT  CGA  GAG  TTC  CGG  TTT  GAT  CTT  TCC  AAG  ATC  CCA  GAA  GGG    594
Tyr  His  His  Arg  Glu  Phe  Arg  Phe  Asp  Leu  Ser  Lys  Ile  Pro  Glu  Gly
                         155                     160                     165

GAA  GCT  GTC  ACG  GCA  GCC  GAA  TTC  CGG  ATC  TAC  AAG  GAC  TAC  ATC  CGG    642
Glu  Ala  Val  Thr  Ala  Ala  Glu  Phe  Arg  Ile  Tyr  Lys  Asp  Tyr  Ile  Arg
               170                      175                     180

GAA  CGC  TTC  GAC  AAT  GAG  ACG  TTC  CGG  ATC  AGC  GTT  TAT  CAG  GTG  CTC    690
Glu  Arg  Phe  Asp  Asn  Glu  Thr  Phe  Arg  Ile  Ser  Val  Tyr  Gln  Val  Leu
     185                      190                     195

CAG  GAG  CAC  TTG  GGC  AGG  GAA  TCG  GAT  CTC  TTC  CTG  CTC  GAC  AGC  CGT    738
Gln  Glu  His  Leu  Gly  Arg  Glu  Ser  Asp  Leu  Phe  Leu  Leu  Asp  Ser  Arg
In   200                      205                     210

ACC  CTC  TGG  GCC  TCG  GAG  GAG  GGC  TGG  CTG  GTG  TTT  GAC  ATC  ACA  GCC    786
Thr  Leu  Trp  Ala  Ser  Glu  Glu  Gly  Trp  Leu  Val  Phe  Asp  Ile  Thr  Ala
215                      220                     225                         230

ACC  AGC  AAC  CAC  TGG  GTG  GTC  AAT  CCG  CGG  CAC  AAC  CTG  GGC  CTG  CAG    834
Thr  Ser  Asn  His  Trp  Val  Val  Asn  Pro  Arg  His  Asn  Leu  Gly  Leu  Gln
                    235                     240                     245

CTC  TCG  GTG  GAG  ACG  CTG  GAT  GGG  CAG  AGC  ATC  AAC  CCC  AAG  TTG  GCG    882
Leu  Ser  Val  Glu  Thr  Leu  Asp  Gly  Gln  Ser  Ile  Asn  Pro  Lys  Leu  Ala
               250                     255                     260

GGC  CTG  ATT  GGG  CGG  CAC  GGG  CCC  CAG  AAC  AAG  CAG  CCC  TTC  ATG  GTG    930
Gly  Leu  Ile  Gly  Arg  His  Gly  Pro  Gln  Asn  Lys  Gln  Pro  Phe  Met  Val
          265                     270                     275

GCT  TTC  TTC  AAG  GCC  ACG  GAG  GTC  CAC  TTC  CGC  AGC  ATC  CGG  TCC  ACG    978
Ala  Phe  Phe  Lys  Ala  Thr  Glu  Val  His  Phe  Arg  Ser  Ile  Arg  Ser  Thr
     280                     285                     290

GGG  AGC  AAA  CAG  CGC  AGC  CAG  AAC  CGC  TCC  AAG  ACG  CCC  AAG  AAC  CAG    1026
Gly  Ser  Lys  Gln  Arg  Ser  Gln  Asn  Arg  Ser  Lys  Thr  Pro  Lys  Asn  Gln
295                      300                     305                         310

GAA  GCC  CTG  CGG  ATG  GCC  AAC  GTG  GCA  GAG  AAC  AGC  AGC  AGC  GAC  CAG    1074
Glu  Ala  Leu  Arg  Met  Ala  Asn  Val  Ala  Glu  Asn  Ser  Ser  Ser  Asp  Gln
                    315                     320                     325

AGG  CAG  GCC  TGT  AAG  AAG  CAC  GAG  CTG  TAT  GTC  AGC  TTC  CGA  GAC  CTG    1122
Arg  Gln  Ala  Cys  Lys  Lys  His  Glu  Leu  Tyr  Val  Ser  Phe  Arg  Asp  Leu
               330                     335                     340

GGC  TGG  CAG  GAC  TGG  ATC  ATC  GCG  CCT  GAA  GGC  TAC  GCC  GCC  TAC  TAC    1170
Gly  Trp  Gln  Asp  Trp  Ile  Ile  Ala  Pro  Glu  Gly  Tyr  Ala  Ala  Tyr  Tyr
```

|       |       |       |       |       | 345   |       |       |       |       | 350   |       |       |       |       | 355   |       |       |      |
|-------|-------|-------|-------|-------|-------|-------|-------|-------|-------|-------|-------|-------|-------|-------|-------|-------|-------|------|
| TGT   | GAG   | GGG   | GAG   | TGT   | GCC   | TTC   | CCT   | CTG   | AAC   | TCC   | TAC   | ATG   | AAC   | GCC   | ACC   |       |       | 1218 |
| Cys   | Glu   | Gly   | Glu   | Cys   | Ala   | Phe   | Pro   | Leu   | Asn   | Ser   | Tyr   | Met   | Asn   | Ala   | Thr   |       |       |      |
|       | 360   |       |       |       | 365   |       |       |       |       | 370   |       |       |       |       |       |       |       |      |
| AAC   | CAC   | GCC   | ATC   | GTG   | CAG   | ACG   | CTG   | GTC   | CAC   | TTC   | ATC   | AAC   | CCG   | GAA   | ACG   |       |       | 1266 |
| Asn   | His   | Ala   | Ile   | Val   | Gln   | Thr   | Leu   | Val   | His   | Phe   | Ile   | Asn   | Pro   | Glu   | Thr   |       |       |      |
| 375   |       |       |       |       | 380   |       |       |       |       | 385   |       |       |       |       | 390   |       |       |      |
| GTG   | CCC   | AAG   | CCC   | TGC   | TGT   | GCG   | CCC   | ACG   | CAG   | CTC   | AAT   | GCC   | ATC   | TCC   | GTC   |       |       | 1314 |
| Val   | Pro   | Lys   | Pro   | Cys   | Cys   | Ala   | Pro   | Thr   | Gln   | Leu   | Asn   | Ala   | Ile   | Ser   | Val   |       |       |      |
|       |       |       |       | 395   |       |       |       |       | 400   |       |       |       |       | 405   |       |       |       |      |
| CTC   | TAC   | TTC   | GAT   | GAC   | AGC   | TCC   | AAC   | GTC   | ATC   | CTG   | AAG   | AAA   | TAC   | AGA   | AAC   |       |       | 1362 |
| Leu   | Tyr   | Phe   | Asp   | Asp   | Ser   | Ser   | Asn   | Val   | Ile   | Leu   | Lys   | Lys   | Tyr   | Arg   | Asn   |       |       |      |
|       |       |       | 410   |       |       |       |       | 415   |       |       |       |       | 420   |       |       |       |       |      |
| ATG   | GTG   | GTC   | CGG   | GCC   | TGT   | GGC   | TGC   | CAC   | TAGCTCCTCC | GAGAATTCAG |       |       |       |       |       |       |       | 1409 |
| Met   | Val   | Val   | Arg   | Ala   | Cys   | Gly   | Cys   | His   |       |       |       |       |       |       |       |       |       |      |
|       |       | 425   |       |       |       |       | 430   |       |       |       |       |       |       |       |       |       |       |      |

ACCCTTTGGG GCCAAGTTTT TCTGGATCCT CCATTGCTC                              1448

( 2 ) INFORMATION FOR SEQ ID NO:6:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | His | Val | Arg | Ser | Leu | Arg | Ala | Ala | Ala | Pro | His | Ser | Phe | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Trp | Ala | Pro | Leu | Phe | Leu | Leu | Arg | Ser | Ala | Leu | Ala | Asp | Phe | Ser |
|     |     |     | 20  |     |     |     |     | 25  |     |     |     |     | 30  |     |     |
| Leu | Asp | Asn | Glu | Val | His | Ser | Ser | Phe | Ile | His | Arg | Arg | Leu | Arg | Ser |
|     |     |     | 35  |     |     |     |     | 40  |     |     |     |     | 45  |     |     |
| Gln | Glu | Arg | Arg | Glu | Met | Gln | Arg | Glu | Ile | Leu | Ser | Ile | Leu | Gly | Leu |
|     | 50  |     |     |     |     | 55  |     |     |     |     | 60  |     |     |     |     |
| Pro | His | Arg | Pro | Arg | Pro | His | Leu | Gln | Gly | Lys | His | Asn | Ser | Ala | Pro |
| 65  |     |     |     |     | 70  |     |     |     |     | 75  |     |     |     |     | 80  |
| Met | Phe | Met | Leu | Asp | Leu | Tyr | Asn | Ala | Met | Ala | Val | Glu | Glu | Gly | Gly |
|     |     |     |     | 85  |     |     |     |     | 90  |     |     |     |     | 95  |     |
| Gly | Pro | Gly | Gly | Gln | Gly | Phe | Ser | Tyr | Pro | Tyr | Lys | Ala | Val | Phe | Ser |
|     |     |     | 100 |     |     |     |     | 105 |     |     |     |     | 110 |     |     |
| Thr | Gln | Gly | Pro | Pro | Leu | Ala | Ser | Leu | Gln | Asp | Ser | His | Phe | Leu | Thr |
|     |     | 115 |     |     |     |     | 120 |     |     |     |     | 125 |     |     |     |
| Asp | Ala | Asp | Met | Val | Met | Ser | Phe | Val | Asn | Leu | Val | Glu | His | Asp | Lys |
|     | 130 |     |     |     |     | 135 |     |     |     |     | 140 |     |     |     |     |
| Glu | Phe | Phe | His | Pro | Arg | Tyr | His | His | Arg | Glu | Phe | Arg | Phe | Asp | Leu |
| 145 |     |     |     |     | 150 |     |     |     |     | 155 |     |     |     |     | 160 |
| Ser | Lys | Ile | Pro | Glu | Gly | Glu | Ala | Val | Thr | Ala | Ala | Glu | Phe | Arg | Ile |
|     |     |     |     | 165 |     |     |     |     | 170 |     |     |     |     | 175 |     |
| Tyr | Lys | Asp | Tyr | Ile | Arg | Glu | Arg | Phe | Asp | Asn | Glu | Thr | Phe | Arg | Ile |
|     |     |     | 180 |     |     |     |     | 185 |     |     |     |     | 190 |     |     |
| Ser | Val | Tyr | Gln | Val | Leu | Gln | Glu | His | Leu | Gly | Arg | Glu | Ser | Asp | Leu |
|     |     | 195 |     |     |     |     | 200 |     |     |     |     | 205 |     |     |     |
| Phe | Leu | Leu | Asp | Ser | Arg | Thr | Leu | Trp | Ala | Ser | Glu | Glu | Gly | Trp | Leu |
|     | 210 |     |     |     |     | 215 |     |     |     |     | 220 |     |     |     |     |
| Val | Phe | Asp | Ile | Thr | Ala | Thr | Ser | Asn | His | Trp | Val | Val | Asn | Pro | Arg |

|  225 |  |  |  | 230 |  |  |  |  | 235 |  |  |  |  | 240 |
|---|---|---|---|---|---|---|---|---|---|---|---|---|---|---|
| His | Asn | Leu | Gly | Leu<br>245 | Gln | Leu | Ser | Val | Glu<br>250 | Thr | Leu | Asp | Gly<br>255 | Gln | Ser |
| Ile | Asn | Pro | Lys<br>260 | Leu | Ala | Gly | Leu | Ile<br>265 | Gly | Arg | His | Gly | Pro<br>270 | Gln | Asn |
| Lys | Gln | Pro<br>275 | Phe | Met | Val | Ala | Phe<br>280 | Phe | Lys | Ala | Thr | Glu<br>285 | Val | His | Phe |
| Arg | Ser<br>290 | Ile | Arg | Ser | Thr | Gly<br>295 | Ser | Lys | Gln | Arg | Ser<br>300 | Gln | Asn | Arg | Ser |
| Lys<br>305 | Thr | Pro | Lys | Asn | Gln<br>310 | Glu | Ala | Leu | Arg | Met<br>315 | Ala | Asn | Val | Ala | Glu<br>320 |
| Asn | Ser | Ser | Ser | Asp<br>325 | Gln | Arg | Gln | Ala | Cys<br>330 | Lys | Lys | His | Glu | Leu<br>335 | Tyr |
| Val | Ser | Phe | Arg<br>340 | Asp | Leu | Gly | Trp | Gln<br>345 | Asp | Trp | Ile | Ile | Ala<br>350 | Pro | Glu |
| Gly | Tyr | Ala<br>355 | Ala | Tyr | Tyr | Cys | Glu<br>360 | Gly | Glu | Cys | Ala | Phe<br>365 | Pro | Leu | Asn |
| Ser | Tyr<br>370 | Met | Asn | Ala | Thr | Asn<br>375 | His | Ala | Ile | Val | Gln<br>380 | Thr | Leu | Val | His |
| Phe<br>385 | Ile | Asn | Pro | Glu | Thr<br>390 | Val | Pro | Lys | Pro | Cys<br>395 | Cys | Ala | Pro | Thr | Gln<br>400 |
| Leu | Asn | Ala | Ile | Ser<br>405 | Val | Leu | Tyr | Phe | Asp<br>410 | Asp | Ser | Ser | Asn | Val<br>415 | Ile |
| Leu | Lys | Lys | Tyr<br>420 | Arg | Asn | Met | Val | Val<br>425 | Arg | Ala | Cys | Gly | Cys<br>430 | His |  |

( 2 ) INFORMATION FOR SEQ ID NO:7:

( i ) SEQUENCE CHARACTERISTICS:
        ( A ) LENGTH: 2923 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( F ) TISSUE TYPE: Human placenta ( v i i ) IMMEDIATE SOURCE:
        ( A ) LIBRARY: Stratagene catalog #
            cDNA library
        ( B ) CLONE: BMP6C35

( v i i i ) POSITION IN GENOME:
        ( C ) UNITS: bp ( i x ) FEATURE:
        ( A ) NAME/KEY: CDS
        ( B ) LOCATION: 160..1701

( i x ) FEATURE:
        ( A ) NAME/KEY: mat_peptide
        ( B ) LOCATION: 1282..1698

( i x ) FEATURE:
        ( A ) NAME/KEY: mRNA
        ( B ) LOCATION: 1..2923

( x i ) SEQUENCE DESCRIPTION: SEQ ID NO:7:

| CGACCATGAG | AGATAAGGAC | TGAGGGCCAG | GAAGGGGAAG | CGAGCCCGCC | GAGAGGTGGC | 60 |
|---|---|---|---|---|---|---|

-continued

| | |
|---|---|
| GGGGACTGCT CACGCCAAGG GCCACAGCGG CCGCGCTCCG GCCTCGCTCC GCCGCTCCAC | 120 |
| GCCTCGCGGG ATCCGCGGGG GCAGCCCGGC CGGGCGGGG ATG CCG GGG CTG GGG<br>                                                                               Met Pro Gly Leu Gly<br>                                                                             -374                    -370 | 174 |
| CGG AGG GCG CAG TGG CTG TGC TGG TGG TGG GGG CTG CTG TGC AGC TGC<br>Arg Arg Ala Gln Trp Leu Cys Trp Trp Trp Gly Leu Leu Cys Ser Cys<br>         -365                         -360                         -355 | 222 |
| TGC GGG CCC CCG CCG CTG CGG CCG CCC TTG CCC GCT GCC GCG GCC GCC<br>Cys Gly Pro Pro Pro Leu Arg Pro Pro Leu Pro Ala Ala Ala Ala Ala<br>        -350                       -345                       -340 | 270 |
| GCC GCC GGG GGG CAG CTG CTG GGG GAC GGC GGG AGC CCC GGC CGC ACG<br>Ala Ala Gly Gly Gln Leu Leu Gly Asp Gly Gly Ser Pro Gly Arg Thr<br>       -335                    -330                      -325 | 318 |
| GAG CAG CCG CCG CCG TCG CCG CAG TCC TCC TCG GGC TTC CTG TAC CGG<br>Glu Gln Pro Pro Pro Ser Pro Gln Ser Ser Ser Gly Phe Leu Tyr Arg<br>   -320                    -315                      -310 | 366 |
| CGG CTC AAG ACG CAG GAG AAG CGG GAG ATG CAG AAG GAG ATC TTG TCG<br>Arg Leu Lys Thr Gln Glu Lys Arg Glu Met Gln Lys Glu Ile Leu Ser<br>-305                 -300                  -295                 -290 | 414 |
| GTG CTG GGG CTC CCG CAC CGG CCC CGG CCC CTG CAC GGC CTC CAA CAG<br>Val Leu Gly Leu Pro His Arg Pro Arg Pro Leu His Gly Leu Gln Gln<br>         -285                   -280                      -275 | 462 |
| CCG CAG CCC CCG GCG CTC CGG CAG CAG GAG GAG CAG CAG CAG CAG CAG<br>Pro Gln Pro Pro Ala Leu Arg Gln Gln Glu Glu Gln Gln Gln Gln Gln<br>       -270                   -265                    -260 | 510 |
| CAG CTG CCT CGC GGA GAG CCC CCT CCC GGG CGA CTG AAG TCC GCG CCC<br>Gln Leu Pro Arg Gly Glu Pro Pro Pro Gly Arg Leu Lys Ser Ala Pro<br>    -255                   -250                    -245 | 558 |
| CTC TTC ATG CTG GAT CTG TAC AAC GCC CTG TCC GCC GAC AAC GAC GAG<br>Leu Phe Met Leu Asp Leu Tyr Asn Ala Leu Ser Ala Asp Asn Asp Glu<br>       -240                   -235                   -230 | 606 |
| GAC GGG GCG TCG GAG GGG GAG AGG CAG CAG TCC TGG CCC CAC GAA GCA<br>Asp Gly Ala Ser Glu Gly Glu Arg Gln Gln Ser Trp Pro His Glu Ala<br>-225                 -220                  -215                 -210 | 654 |
| GCC AGC TCG TCC CAG CGT CGG CAG CCG CCC CCG GGC GCC GCG CAC CCG<br>Ala Ser Ser Ser Gln Arg Arg Gln Pro Pro Pro Gly Ala Ala His Pro<br>           -205                -200                    -195 | 702 |
| CTC AAC CGC AAG AGC CTT CTG GCC CCC GGA TCT GGC AGC GGC GGC GCG<br>Leu Asn Arg Lys Ser Leu Leu Ala Pro Gly Ser Gly Ser Gly Gly Ala<br>        -190                   -185                    -180 | 750 |
| TCC CCA CTG ACC AGC GCG CAG GAC AGC GCC TTC CTC AAC GAC GCG GAC<br>Ser Pro Leu Thr Ser Ala Gln Asp Ser Ala Phe Leu Asn Asp Ala Asp<br>      -175                   -170                    -165 | 798 |
| ATG GTC ATG AGC TTT GTG AAC CTG GTG GAG TAC GAC AAG GAG TTC TCC<br>Met Val Met Ser Phe Val Asn Leu Val Glu Tyr Asp Lys Glu Phe Ser<br>-160                -155                  -150 | 846 |
| CCT CGT CAG CGA CAC CAC AAA GAG TTC AAG TTC AAC TTA TCC CAG ATT<br>Pro Arg Gln Arg His His Lys Glu Phe Lys Phe Asn Leu Ser Gln Ile<br>-145                -140                 -135                -130 | 894 |
| CCT GAG GGT GAG GTG GTG ACG GCT GCA GAA TTC CGC ATC TAC AAG GAC<br>Pro Glu Gly Glu Val Val Thr Ala Ala Glu Phe Arg Ile Tyr Lys Asp<br>          -125                 -120                  -115 | 942 |
| TGT GTT ATG GGG AGT TTT AAA AAC CAA ACT TTT CTT ATC AGC ATT TAT<br>Cys Val Met Gly Ser Phe Lys Asn Gln Thr Phe Leu Ile Ser Ile Tyr<br>       -110                   -105                    -100 | 990 |
| CAA GTC TTA CAG GAG CAT CAG CAC AGA GAC TCT GAC CTG TTT TTG TTG<br>Gln Val Leu Gln Glu His Gln His Arg Asp Ser Asp Leu Phe Leu Leu<br>    -95                 -90                   -85 | 1038 |
| GAC ACC CGT GTA GTA TGG GCC TCA GAA GAA GGC TGG CTG GAA TTT GAC | 1086 |

| | | | | | | | | | | | | | | |
|---|---|---|---|---|---|---|---|---|---|---|---|---|---|---|
| Asp | Thr | Arg | Val | Val | Trp | Ala | Ser | Glu | Glu | Gly | Trp | Leu | Glu | Phe | Asp |
| | -80 | | | | -75 | | | | | -70 | | | | |

| ATC | ACG | GCC | ACT | AGC | AAT | CTG | TGG | GTT | GTG | ACT | CCA | CAG | CAT | AAC | ATG | 1134 |
| Ile | Thr | Ala | Thr | Ser | Asn | Leu | Trp | Val | Val | Thr | Pro | Gln | His | Asn | Met |
| -65 | | | | | -60 | | | | | -55 | | | | | -50 |

| GGG | CTT | CAG | CTG | AGC | GTG | GTG | ACA | AGG | GAT | GGA | GTC | CAC | GTC | CAC | CCC | 1182 |
| Gly | Leu | Gln | Leu | Ser | Val | Val | Thr | Arg | Asp | Gly | Val | His | Val | His | Pro |
| | | | | -45 | | | | | -40 | | | | | -35 | |

| CGA | GCC | GCA | GGC | CTG | GTG | GGC | AGA | GAC | GGC | CCT | TAC | GAT | AAG | CAG | CCC | 1230 |
| Arg | Ala | Ala | Gly | Leu | Val | Gly | Arg | Asp | Gly | Pro | Tyr | Asp | Lys | Gln | Pro |
| | | | -30 | | | | | -25 | | | | | -20 | | |

| TTC | ATG | GTG | GCT | TTC | TTC | AAA | GTG | AGT | GAG | GTC | CAC | GTG | CGC | ACC | ACC | 1278 |
| Phe | Met | Val | Ala | Phe | Phe | Lys | Val | Ser | Glu | Val | His | Val | Arg | Thr | Thr |
| | -15 | | | | | -10 | | | | | -5 | | | | |

| AGG | TCA | GCC | TCC | AGC | CGG | CGC | CGA | CAA | CAG | AGT | CGT | AAT | CGC | TCT | ACC | 1326 |
| Arg | Ser | Ala | Ser | Ser | Arg | Arg | Arg | Gln | Gln | Ser | Arg | Asn | Arg | Ser | Thr |
| | 1 | | | | 5 | | | | | 10 | | | | | 15 |

| CAG | TCC | CAG | GAC | GTG | GCG | CGG | GTC | TCC | AGT | GCT | TCA | GAT | TAC | AAC | AGC | 1374 |
| Gln | Ser | Gln | Asp | Val | Ala | Arg | Val | Ser | Ser | Ala | Ser | Asp | Tyr | Asn | Ser |
| | | | | 20 | | | | | 25 | | | | | 30 | |

| AGT | GAA | TTG | AAA | ACA | GCC | TGC | AGG | AAG | CAT | GAG | CTG | TAT | GTG | AGT | TTC | 1422 |
| Ser | Glu | Leu | Lys | Thr | Ala | Cys | Arg | Lys | His | Glu | Leu | Tyr | Val | Ser | Phe |
| | | | 35 | | | | | 40 | | | | | 45 | | |

| CAA | GAC | CTG | GGA | TGG | CAG | GAC | TGG | ATC | ATT | GCA | CCC | AAG | GGC | TAT | GCT | 1470 |
| Gln | Asp | Leu | Gly | Trp | Gln | Asp | Trp | Ile | Ile | Ala | Pro | Lys | Gly | Tyr | Ala |
| | | 50 | | | | | 55 | | | | | 60 | | | |

| GCC | AAT | TAC | TGT | GAT | GGA | GAA | TGC | TCC | TTC | CCA | CTC | AAC | GCA | CAC | ATG | 1518 |
| Ala | Asn | Tyr | Cys | Asp | Gly | Glu | Cys | Ser | Phe | Pro | Leu | Asn | Ala | His | Met |
| | 65 | | | | | 70 | | | | | 75 | | | | |

| AAT | GCA | ACC | AAC | CAC | GCG | ATT | GTG | CAG | ACC | TTG | GTT | CAC | CTT | ATG | AAC | 1566 |
| Asn | Ala | Thr | Asn | His | Ala | Ile | Val | Gln | Thr | Leu | Val | His | Leu | Met | Asn |
| 80 | | | | | 85 | | | | | 90 | | | | | 95 |

| CCC | GAG | TAT | GTC | CCC | AAA | CCG | TGC | TGT | GCG | CCA | ACT | AAG | CTA | AAT | GCC | 1614 |
| Pro | Glu | Tyr | Val | Pro | Lys | Pro | Cys | Cys | Ala | Pro | Thr | Lys | Leu | Asn | Ala |
| | | | | 100 | | | | | 105 | | | | | 110 | |

| ATC | TCG | GTT | CTT | TAC | TTT | GAT | GAC | AAC | TCC | AAT | GTC | ATT | CTG | AAA | AAA | 1662 |
| Ile | Ser | Val | Leu | Tyr | Phe | Asp | Asp | Asn | Ser | Asn | Val | Ile | Leu | Lys | Lys |
| | | | 115 | | | | | 120 | | | | | 125 | | |

| TAC | AGG | AAT | ATG | GTT | GTA | AGA | GCT | TGT | GGA | TGC | CAC | TAACTCGAAA | | | | 1708 |
| Tyr | Arg | Asn | Met | Val | Val | Arg | Ala | Cys | Gly | Cys | His | |
| | 130 | | | | | 135 | | | | | 140 | |

| CCAGATGCTG | GGGACACACA | TTCTGCCTTG | GATTCCTAGA | TTACATCTGC | CTTAAAAAAA | 1768 |
| CACGGAAGCA | CAGTTGGAGG | TGGGACGATG | AGACTTTGAA | ACTATCTCAT | GCCAGTGCCT | 1828 |
| TATTACCCAG | GAAGATTTTA | AAGGACCTCA | TTAATAATTT | GCTCACTTGG | TAAATGACGT | 1888 |
| GAGTAGTTGT | TGGTCTGTAG | CAAGCTGAGT | TTGGATGTCT | GTAGCATAAG | GTCTGGTAAC | 1948 |
| TGCAGAAACA | TAACCGTGAA | GCTCTTCCTA | CCCTCCTCCC | CCAAAACCC | ACCAAAATTA | 2008 |
| GTTTTAGCTG | TAGATCAAGC | TATTTGGGGT | GTTTGTTAGT | AAATAGGGAA | ATAATCTCA | 2068 |
| AAGGAGTTAA | ATGTATTCTT | GGCTAAAGGA | TCAGCTGGTT | CAGTACTGTC | TATCAAAGGT | 2128 |
| AGATTTTACA | GAGAACAGAA | ATCGGGGAAG | TGGGGGGAAC | GCCTCTGTTC | AGTTCATTCC | 2188 |
| CAGAAGTCCA | CAGGACGCAC | AGCCCAGGCC | ACAGCCAGGG | CTCCACGGGG | CGCCCTTGTC | 2248 |
| TCAGTCATTG | CTGTTGTATG | TTCGTGCTGG | AGTTTTGTTG | GTGTGAAAAT | ACACTTATTT | 2308 |
| CAGCCAAAAC | ATACCATTTC | TACACCTCAA | TCCTCCATTT | GCTGTACTCT | TTGCTAGTAC | 2368 |
| CAAAAGTAGA | CTGATTACAC | TGAGGTGAGG | CTACAAGGGG | TGTGTAACCG | TGTAACACGT | 2428 |

| | | | | |
|---|---|---|---|---|
| GAAGGCAGTG | CTCACCTCTT | CTTTACCAGA | ACGGTTCTTT | GACCAGCACA | TTAACTTCTG | 2488 |
| GACTGCCGGC | TCTAGTACCT | TTTCAGTAAA | GTGGTTCTCT | GCCTTTTTAC | TATACAGCAT | 2548 |
| ACCACGCCAC | AGGGTTAGAA | CCAACGAAGA | AAATAAAATG | AGGGTGCCCA | GCTTATAAGA | 2608 |
| ATGGTGTTAG | GGGGATGAGC | ATGCTGTTTA | TGAACGGAAA | TCATGATTTC | CCTGTAGAAA | 2668 |
| GTGAGGCTCA | GATTAAATTT | TAGAATATTT | TCTAAATGTC | TTTTTCACAA | TCATGTGACT | 2728 |
| GGGAAGGCAA | TTTCATACTA | AACTGATTAA | ATAATACATT | TATAATCTAC | AACTGTTTGC | 2788 |
| ACTTACAGCT | TTTTTTGTAA | ATATAAACTA | TAATTTATTG | TCTATTTTAT | ATCTGTTTTG | 2848 |
| CTGTGGCGTT | GGGGGGGGGG | CCGGGCTTTT | GGGGGGGGGG | GTTTGTTTGG | GGGGTGTCGT | 2908 |
| GGTGTGGGCG | GGCGG | | | | | 2923 |

( 2 ) INFORMATION FOR SEQ ID NO:8:

( i ) SEQUENCE CHARACTERISTICS:
( A ) LENGTH: 513 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met  Pro  Gly  Leu  Gly  Arg  Arg  Ala  Gln  Trp  Leu  Cys  Trp  Trp  Trp  Gly
-374           -370                     -365                     -360

Leu  Leu  Cys  Ser  Cys  Cys  Gly  Pro  Pro  Leu  Arg  Pro  Pro  Leu  Pro
          -355                -350                          -345

Ala  Ala  Ala  Ala  Ala  Ala  Ala  Gly  Gly  Gln  Leu  Leu  Gly  Asp  Gly  Gly
     -340                     -335                     -330

Ser  Pro  Gly  Arg  Thr  Glu  Gln  Pro  Pro  Ser  Pro  Gln  Ser  Ser  Ser
     -325                -320                     -315

Gly  Phe  Leu  Tyr  Arg  Arg  Leu  Lys  Thr  Gln  Glu  Lys  Arg  Glu  Met  Gln
-310           -305                     -300                     -295

Lys  Glu  Ile  Leu  Ser  Val  Leu  Gly  Leu  Pro  His  Arg  Pro  Arg  Pro  Leu
               -290                     -285                     -280

His  Gly  Leu  Gln  Gln  Pro  Gln  Pro  Pro  Ala  Leu  Arg  Gln  Gln  Glu  Glu
          -275                     -270                     -265

Gln  Gln  Gln  Gln  Gln  Gln  Leu  Pro  Arg  Gly  Glu  Pro  Pro  Pro  Gly  Arg
     -260                     -255                     -250

Leu  Lys  Ser  Ala  Pro  Leu  Phe  Met  Leu  Asp  Leu  Tyr  Asn  Ala  Leu  Ser
     -245                -240                     -235

Ala  Asp  Asn  Asp  Glu  Asp  Gly  Ala  Ser  Glu  Gly  Glu  Arg  Gln  Gln  Ser
-230                -225                     -220                     -215

Trp  Pro  His  Glu  Ala  Ala  Ser  Ser  Ser  Gln  Arg  Arg  Gln  Pro  Pro  Pro
          -210                     -205                     -200

Gly  Ala  Ala  His  Pro  Leu  Asn  Arg  Lys  Ser  Leu  Leu  Ala  Pro  Gly  Ser
               -195                     -190                     -185

Gly  Ser  Gly  Gly  Ala  Ser  Pro  Leu  Thr  Ser  Ala  Gln  Asp  Ser  Ala  Phe
          -180                     -175                     -170

Leu  Asn  Asp  Ala  Asp  Met  Val  Met  Ser  Phe  Val  Asn  Leu  Val  Glu  Tyr
     -165                -160                     -155

Asp  Lys  Glu  Phe  Ser  Pro  Arg  Gln  Arg  His  His  Lys  Glu  Phe  Lys  Phe
-150                -145                     -140                     -135

Asn  Leu  Ser  Gln  Ile  Pro  Glu  Gly  Glu  Val  Val  Thr  Ala  Ala  Glu  Phe
               -130                     -125                     -120

Arg  Ile  Tyr  Lys  Asp  Cys  Val  Met  Gly  Ser  Phe  Lys  Asn  Gln  Thr  Phe
```

|      |      |      | -115 |      |      |      | -110 |      |      |      | -105 |      |      |      |
|------|------|------|------|------|------|------|------|------|------|------|------|------|------|------|
| Leu  | Ile  | Ser  | Ile  | Tyr  | Gln  | Val  | Leu  | Gln  | Glu  | His  | Gln  | His  | Arg  | Asp  | Ser |
|      |      | -100 |      |      |      |      | -95  |      |      |      |      | -90  |      |      |

```
        - 1 1 5                          - 1 1 0                          - 1 0 5
Leu  Ile  Ser  Ile  Tyr  Gln  Val  Leu  Gln  Glu  His  Gln  His  Arg  Asp  Ser
          -100                      -95                      -90

Asp  Leu  Phe  Leu  Leu  Asp  Thr  Arg  Val  Val  Trp  Ala  Ser  Glu  Glu  Gly
     -85                      -80                 -75

Trp  Leu  Glu  Phe  Asp  Ile  Thr  Ala  Thr  Ser  Asn  Leu  Trp  Val  Val  Thr
-70                       -65                      -60                          -55

Pro  Gln  His  Asn  Met  Gly  Leu  Gln  Leu  Ser  Val  Val  Thr  Arg  Asp  Gly
               -50                      -45                           -40

Val  His  Val  His  Pro  Arg  Ala  Ala  Gly  Leu  Val  Gly  Arg  Asp  Gly  Pro
               -35                 -30                           -25

Tyr  Asp  Lys  Gln  Pro  Phe  Met  Val  Ala  Phe  Phe  Lys  Val  Ser  Glu  Val
          -20                 -15                           -10

His  Val  Arg  Thr  Thr  Arg  Ser  Ala  Ser  Ser  Arg  Arg  Arg  Gln  Gln  Ser
     -5                        1                      5                            10

Arg  Asn  Arg  Ser  Thr  Gln  Ser  Gln  Asp  Val  Ala  Arg  Val  Ser  Ser  Ala
                15                      20                           25

Ser  Asp  Tyr  Asn  Ser  Ser  Glu  Leu  Lys  Thr  Ala  Cys  Arg  Lys  His  Glu
               30                      35                           40

Leu  Tyr  Val  Ser  Phe  Gln  Asp  Leu  Gly  Trp  Gln  Asp  Trp  Ile  Ile  Ala
          45                      50                           55

Pro  Lys  Gly  Tyr  Ala  Ala  Asn  Tyr  Cys  Asp  Gly  Glu  Cys  Ser  Phe  Pro
     60                       65                      70

Leu  Asn  Ala  His  Met  Asn  Ala  Thr  Asn  His  Ala  Ile  Val  Gln  Thr  Leu
75                       80                      85                            90

Val  His  Leu  Met  Asn  Pro  Glu  Tyr  Val  Pro  Lys  Pro  Cys  Cys  Ala  Pro
               95                       100                      105

Thr  Lys  Leu  Asn  Ala  Ile  Ser  Val  Leu  Tyr  Phe  Asp  Asp  Asn  Ser  Asn
               110                      115                      120

Val  Ile  Leu  Lys  Lys  Tyr  Arg  Asn  Met  Val  Val  Arg  Ala  Cys  Gly  Cys
               125                      130                      135

His
```

( 2 ) INFORMATION FOR SEQ ID NO:9:

( i ) SEQUENCE CHARACTERISTICS:
        ( A ) LENGTH: 2153 base pairs
        ( B ) TYPE: nucleic acid
        ( C ) STRANDEDNESS: double
        ( D ) TOPOLOGY: linear ( i i i ) HYPOTHETICAL: NO ( v i ) ORIGINAL SOURCE:
        ( A ) ORGANISM: Homo sapiens
        ( H ) CELL LINE: U2-OS osteosarcoma ( v i i ) IMMEDIATE SOURCE:
        ( A ) LIBRARY: U2-OS human osteosarcoma cDNA library
        ( B ) CLONE: U2-16

( v i i i ) POSITION IN GENOME:
        ( C ) UNITS: bp ( i x ) FEATURE:
        ( A ) NAME/KEY: CDS
        ( B ) LOCATION: 699..2063

( i x ) FEATURE:
        ( A ) NAME/KEY: mat_peptide
        ( B ) LOCATION: 1647..2060

( i x ) FEATURE:
( A ) NAME/KEY: mRNA
( B ) LOCATION: 1..2153

( x i ) SEQUENCE DESCRIPTION: SEQ ID NO:9:

| | | | | |
|---|---|---|---|---|
| CTGGTATATT | TGTGCCTGCT | GGAGGTGGAA | TTAACAGTAA | GAAGGAGAAA | GGGATTGAAT | 60 |
| GGACTTACAG | GAAGGATTTC | AAGTAAATTC | AGGGAAACAC | ATTTACTTGA | ATAGTACAAC | 120 |
| CTAGAGTATT | ATTTTACACT | AAGACGACAC | AAAAGATGTT | AAAGTTATCA | CCAAGCTGCC | 180 |
| GGACAGATAT | ATATTCCAAC | ACCAAGGTGC | AGATCAGCAT | AGATCTGTGA | TTCAGAAATC | 240 |
| AGGATTTGTT | TTGGAAAGAG | CTCAAGGGTT | GAGAAGAACT | CAAAAGCAAG | TGAAGATTAC | 300 |
| TTTGGGAACT | ACAGTTTATC | AGAAGATCAA | CTTTTGCTAA | TTCAAATACC | AAAGGCCTGA | 360 |
| TTATCATAAA | TTCATATAGG | AATGCATAGG | TCATCTGATC | AAATAATATT | AGCCGTCTTC | 420 |
| TGCTACATCA | ATGCAGCAAA | AACTCTTAAC | AACTGTGGAT | AATTGGAAAT | CTGAGTTTCA | 480 |
| GCTTCTTAG | AAATAACTAC | TCTTGACATA | TTCCAAAATA | TTTAAAATAG | GACAGGAAAA | 540 |
| TCGGTGAGGA | TGTTGTGCTC | AGAAATGTCA | CTGTCATGAA | AAATAGGTAA | ATTTGTTTTT | 600 |
| TCAGCTACTG | GGAAACTGTA | CCTCCTAGAA | CCTTAGGTTT | TTTTTTTTT | AAGAGGACAA | 660 |
| GAAGGACTAA | AAATATCAAC | TTTTGCTTTT | GGACAAAA | ATG CAT CTG ACT GTA | | 713 |
| | | | | Met His Leu Thr Val | |
| | | | | -316 -315 | |

```
TTT TTA CTT AAG GGT ATT GTG GGT TTC CTC TGG AGC TGC TGG GTT CTA          761
Phe Leu Leu Lys Gly Ile Val Gly Phe Leu Trp Ser Cys Trp Val Leu
    -310              -305              -300

GTG GGT TAT GCA AAA GGA GGT TTG GGA GAC AAT CAT GTT CAC TCC AGT          809
Val Gly Tyr Ala Lys Gly Gly Leu Gly Asp Asn His Val His Ser Ser
-295              -290              -285              -280

TTT ATT TAT AGA AGA CTA CGG AAC CAC GAA AGA CGG GAA ATA CAA AGG          857
Phe Ile Tyr Arg Arg Leu Arg Asn His Glu Arg Arg Glu Ile Gln Arg
        -275              -270              -265

GAA ATT CTC TCT ATC TTG GGT TTG CCT CAC AGA CCC AGA CCA TTT TCA          905
Glu Ile Leu Ser Ile Leu Gly Leu Pro His Arg Pro Arg Pro Phe Ser
            -260              -255              -250

CCT GGA AAA ATG ACC AAT CAA GCG TCC TCT GCA CCT CTC TTT ATG CTG          953
Pro Gly Lys Met Thr Asn Gln Ala Ser Ser Ala Pro Leu Phe Met Leu
        -245              -240              -235

GAT CTC TAC AAT GCC GAA GAA AAT CCT GAA GAG TCG GAG TAC TCA GTA         1001
Asp Leu Tyr Asn Ala Glu Glu Asn Pro Glu Glu Ser Glu Tyr Ser Val
    -230              -225              -220

AGG GCA TCC TTG GCA GAA GAG ACC AGA GGG GCA AGA AAG GGA TAC CCA         1049
Arg Ala Ser Leu Ala Glu Glu Thr Arg Gly Ala Arg Lys Gly Tyr Pro
-215              -210              -205              -200

GCC TCT CCC AAT GGG TAT CCT CGT CGC ATA CAG TTA TCT CGG ACG ACT         1097
Ala Ser Pro Asn Gly Tyr Pro Arg Arg Ile Gln Leu Ser Arg Thr Thr
        -195              -190              -185

CCT CTG ACC ACC CAG AGT CCT CCT CTA GCC AGC CTC CAT GAT ACC AAC         1145
Pro Leu Thr Thr Gln Ser Pro Pro Leu Ala Ser Leu His Asp Thr Asn
        -180              -175              -170

TTT CTG AAT GAT GCT GAC ATG GTC ATG AGC TTT GTC AAC TTA GTT GAA         1193
Phe Leu Asn Asp Ala Asp Met Val Met Ser Phe Val Asn Leu Val Glu
    -165              -160              -155

AGA GAC AAG GAT TTT TCT CAC CAG CGA AGG CAT TAC AAA GAA TTT CGA         1241
Arg Asp Lys Asp Phe Ser His Gln Arg Arg His Tyr Lys Glu Phe Arg
-150              -145              -140

TTT GAT CTT ACC CAA ATT CCT CAT GGA GAG GCA GTG ACA GCA GCT GAA         1289
Phe Asp Leu Thr Gln Ile Pro His Gly Glu Ala Val Thr Ala Ala Glu
-135              -130              -125              -120
```

-continued

| | | | | | | | | | | | | | | | | |
|---|---|---|---|---|---|---|---|---|---|---|---|---|---|---|---|---|
| TTC | CGG | ATA | TAC | AAG | GAC | CGG | AGC | AAC | AAC | CGA | TTT | GAA | AAT | GAA | ACA | 1337 |
| Phe | Arg | Ile | Tyr | Lys | Asp | Arg | Ser | Asn | Asn | Arg | Phe | Glu | Asn | Glu | Thr | |
| | | | -115 | | | | | -110 | | | | | | -105 | | |
| ATT | AAG | ATT | AGC | ATA | TAT | CAA | ATC | ATC | AAG | GAA | TAC | ACA | AAT | AGG | GAT | 1385 |
| Ile | Lys | Ile | Ser | Ile | Tyr | Gln | Ile | Ile | Lys | Glu | Tyr | Thr | Asn | Arg | Asp | |
| | | | -100 | | | | | -95 | | | | | -90 | | | |
| GCA | GAT | CTG | TTC | TTG | TTA | GAC | ACA | AGA | AAG | GCC | CAA | GCT | TTA | GAT | GTG | 1433 |
| Ala | Asp | Leu | Phe | Leu | Leu | Asp | Thr | Arg | Lys | Ala | Gln | Ala | Leu | Asp | Val | |
| | | -85 | | | | | -80 | | | | | -75 | | | | |
| GGT | TGG | CTT | GTC | TTT | GAT | ATC | ACT | GTG | ACC | AGC | AAT | CAT | TGG | GTG | ATT | 1481 |
| Gly | Trp | Leu | Val | Phe | Asp | Ile | Thr | Val | Thr | Ser | Asn | His | Trp | Val | Ile | |
| | -70 | | | | | -65 | | | | | -60 | | | | | |
| AAT | CCC | CAG | AAT | AAT | TTG | GGC | TTA | CAG | CTC | TGT | GCA | GAA | ACA | GGG | GAT | 1529 |
| Asn | Pro | Gln | Asn | Asn | Leu | Gly | Leu | Gln | Leu | Cys | Ala | Glu | Thr | Gly | Asp | |
| -55 | | | | | -50 | | | | | -45 | | | | | -40 | |
| GGA | CGC | AGT | ATC | AAC | GTA | AAA | TCT | GCT | GGT | CTT | GTG | GGA | AGA | CAG | GGA | 1577 |
| Gly | Arg | Ser | Ile | Asn | Val | Lys | Ser | Ala | Gly | Leu | Val | Gly | Arg | Gln | Gly | |
| | | | | -35 | | | | | -30 | | | | | -25 | | |
| CCT | CAG | TCA | AAA | CAA | CCA | TTC | ATG | GTG | GCC | TTC | TTC | AAG | GCG | AGT | GAG | 1625 |
| Pro | Gln | Ser | Lys | Gln | Pro | Phe | Met | Val | Ala | Phe | Phe | Lys | Ala | Ser | Glu | |
| | | | -20 | | | | | -15 | | | | | -10 | | | |
| GTA | CTT | CTT | CGA | TCC | GTG | AGA | GCA | GCC | AAC | AAA | CGA | AAA | AAT | CAA | AAC | 1673 |
| Val | Leu | Leu | Arg | Ser | Val | Arg | Ala | Ala | Asn | Lys | Arg | Lys | Asn | Gln | Asn | |
| | | -5 | | | | | 1 | | | | 5 | | | | | |
| CGC | AAT | AAA | TCC | AGC | TCT | CAT | CAG | GAC | TCC | TCC | AGA | ATG | TCC | AGT | GTT | 1721 |
| Arg | Asn | Lys | Ser | Ser | Ser | His | Gln | Asp | Ser | Ser | Arg | Met | Ser | Ser | Val | |
| 10 | | | | | 15 | | | | | 20 | | | | | 25 | |
| GGA | GAT | TAT | AAC | ACA | AGT | GAG | CAA | AAA | CAA | GCC | TGT | AAG | AAG | CAC | GAA | 1769 |
| Gly | Asp | Tyr | Asn | Thr | Ser | Glu | Gln | Lys | Gln | Ala | Cys | Lys | Lys | His | Glu | |
| | | | | 30 | | | | | 35 | | | | | 40 | | |
| CTC | TAT | GTG | AGC | TTC | CGG | GAT | CTG | GGA | TGG | CAG | GAC | TGG | ATT | ATA | GCA | 1817 |
| Leu | Tyr | Val | Ser | Phe | Arg | Asp | Leu | Gly | Trp | Gln | Asp | Trp | Ile | Ile | Ala | |
| | | | 45 | | | | | 50 | | | | | 55 | | | |
| CCA | GAA | GGA | TAC | GCT | GCA | TTT | TAT | TGT | GAT | GGA | GAA | TGT | TCT | TTT | CCA | 1865 |
| Pro | Glu | Gly | Tyr | Ala | Ala | Phe | Tyr | Cys | Asp | Gly | Glu | Cys | Ser | Phe | Pro | |
| | | 60 | | | | | 65 | | | | | 70 | | | | |
| CTT | AAC | GCC | CAT | ATG | AAT | GCC | ACC | AAC | CAC | GCT | ATA | GTT | CAG | ACT | CTG | 1913 |
| Leu | Asn | Ala | His | Met | Asn | Ala | Thr | Asn | His | Ala | Ile | Val | Gln | Thr | Leu | |
| | 75 | | | | | 80 | | | | | 85 | | | | | |
| GTT | CAT | CTG | ATG | TTT | CCT | GAC | CAC | GTA | CCA | AAG | CCT | TGT | TGT | GCT | CCA | 1961 |
| Val | His | Leu | Met | Phe | Pro | Asp | His | Val | Pro | Lys | Pro | Cys | Cys | Ala | Pro | |
| 90 | | | | | 95 | | | | | 100 | | | | | 105 | |
| ACC | AAA | TTA | AAT | GCC | ATC | TCT | GTT | CTG | TAC | TTT | GAT | GAC | AGC | TCC | AAT | 2009 |
| Thr | Lys | Leu | Asn | Ala | Ile | Ser | Val | Leu | Tyr | Phe | Asp | Asp | Ser | Ser | Asn | |
| | | | | 110 | | | | | 115 | | | | | 120 | | |
| GTC | ATT | TTG | AAA | AAA | TAT | AGA | AAT | ATG | GTA | GTA | CGC | TCA | TGT | GGC | TGC | 2057 |
| Val | Ile | Leu | Lys | Lys | Tyr | Arg | Asn | Met | Val | Val | Arg | Ser | Cys | Gly | Cys | |
| | | | 125 | | | | | 130 | | | | | 135 | | | |
| CAC | TAATATTAAA | TAATATTGAT | AATAACAAAA | AGATCTGTAT | TAAGGTTTAT | | | | | | | | | | | 2110 |
| His | | | | | | | | | | | | | | | | |
| GGCTGCAATA | AAAAGCATAC | TTTCAGACAA | ACAGAAAAAA | AAA | | | | | | | | | | | | 2153 |

( 2 ) INFORMATION FOR SEQ ID NO:10:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | His | Leu | Thr | Val | Phe | Leu | Leu | Lys | Gly | Ile | Val | Gly | Phe | Leu | Trp |
|-316|-315|    |    |    |-310|    |    |    |    |-305|    |    |    |    |    |

| Ser | Cys | Trp | Val | Leu | Val | Gly | Tyr | Ala | Lys | Gly | Gly | Leu | Gly | Asp | Asn |
|-300|    |    |    |    |-295|    |    |    |    |-290|    |    |    |    |-285|

| His | Val | His | Ser | Ser | Phe | Ile | Tyr | Arg | Arg | Leu | Arg | Asn | His | Glu | Arg |
|    |    |    |    |-280|    |    |    |    |-275|    |    |    |    |-270|    |

| Arg | Glu | Ile | Gln | Arg | Glu | Ile | Leu | Ser | Ile | Leu | Gly | Leu | Pro | His | Arg |
|    |    |    |-265|    |    |    |    |-260|    |    |    |    |-255|    |    |

| Pro | Arg | Pro | Phe | Ser | Pro | Gly | Lys | Met | Thr | Asn | Gln | Ala | Ser | Ser | Ala |
|    |    |-250|    |    |    |    |-245|    |    |    |    |-240|    |    |    |

| Pro | Leu | Phe | Met | Leu | Asp | Leu | Tyr | Asn | Ala | Glu | Glu | Asn | Pro | Glu | Glu |
|    |-235|    |    |    |    |-230|    |    |    |    |-225|    |    |    |    |

| Ser | Glu | Tyr | Ser | Val | Arg | Ala | Ser | Leu | Ala | Glu | Glu | Thr | Arg | Gly | Ala |
|-220|    |    |    |    |-215|    |    |    |    |-210|    |    |    |    |-205|

| Arg | Lys | Gly | Tyr | Pro | Ala | Ser | Pro | Asn | Gly | Tyr | Pro | Arg | Arg | Ile | Gln |
|    |    |    |    |-200|    |    |    |    |-195|    |    |    |    |-190|    |

| Leu | Ser | Arg | Thr | Thr | Pro | Leu | Thr | Thr | Gln | Ser | Pro | Pro | Leu | Ala | Ser |
|    |    |    |-185|    |    |    |    |-180|    |    |    |    |-175|    |    |

| Leu | His | Asp | Thr | Asn | Phe | Leu | Asn | Asp | Ala | Asp | Met | Val | Met | Ser | Phe |
|    |    |    |-170|    |    |    |-165|    |    |    |    |-160|    |    |    |

| Val | Asn | Leu | Val | Glu | Arg | Asp | Lys | Asp | Phe | Ser | His | Gln | Arg | Arg | His |
|    |-155|    |    |    |    |-150|    |    |    |    |-145|    |    |    |    |

| Tyr | Lys | Glu | Phe | Arg | Phe | Asp | Leu | Thr | Gln | Ile | Pro | His | Gly | Glu | Ala |
|-140|    |    |    |    |-135|    |    |    |    |-130|    |    |    |    |-125|

| Val | Thr | Ala | Ala | Glu | Phe | Arg | Ile | Tyr | Lys | Asp | Arg | Ser | Asn | Asn | Arg |
|    |    |    |    |-120|    |    |    |    |-115|    |    |    |    |-110|    |

| Phe | Glu | Asn | Glu | Thr | Ile | Lys | Ile | Ser | Ile | Tyr | Gln | Ile | Ile | Lys | Glu |
|    |    |    |    |-105|    |    |    |    |-100|    |    |    |    |-95 |    |

| Tyr | Thr | Asn | Arg | Asp | Ala | Asp | Leu | Phe | Leu | Leu | Asp | Thr | Arg | Lys | Ala |
|    |    |    |-90 |    |    |    |    |-85 |    |    |    |    |-80 |    |    |

| Gln | Ala | Leu | Asp | Val | Gly | Trp | Leu | Val | Phe | Asp | Ile | Thr | Val | Thr | Ser |
|    |-75 |    |    |    |    |-70 |    |    |    |    |-65 |    |    |    |    |

| Asn | His | Trp | Val | Ile | Asn | Pro | Gln | Asn | Asn | Leu | Gly | Leu | Gln | Leu | Cys |
|-60 |    |    |    |    |-55 |    |    |    |    |-50 |    |    |    |    |-45 |

| Ala | Glu | Thr | Gly | Asp | Gly | Arg | Ser | Ile | Asn | Val | Lys | Ser | Ala | Gly | Leu |
|    |    |    |    |-40 |    |    |    |    |-35 |    |    |    |    |    |-30 |

| Val | Gly | Arg | Gln | Gly | Pro | Gln | Ser | Lys | Gln | Pro | Phe | Met | Val | Ala | Phe |
|    |    |    |-25 |    |    |    |    |-20 |    |    |    |    |-15 |    |    |

| Phe | Lys | Ala | Ser | Glu | Val | Leu | Leu | Arg | Ser | Val | Arg | Ala | Ala | Asn | Lys |
|    |    |    |-10 |    |    |    |    |-5  |    |    |    |    |    |1   |    |

| Arg | Lys | Asn | Gln | Asn | Arg | Asn | Lys | Ser | Ser | Ser | His | Gln | Asp | Ser | Ser |
|5   |    |    |    |    |10  |    |    |    |    |15  |    |    |    |    |20  |

| Arg | Met | Ser | Ser | Val | Gly | Asp | Tyr | Asn | Thr | Ser | Glu | Gln | Lys | Gln | Ala |
|    |    |    |    |25  |    |    |    |    |30  |    |    |    |    |35  |    |

| Cys | Lys | Lys | His | Glu | Leu | Tyr | Val | Ser | Phe | Arg | Asp | Leu | Gly | Trp | Gln |
|    |    |    |40  |    |    |    |    |45  |    |    |    |    |50  |    |    |

| Asp | Trp | Ile | Ile | Ala | Pro | Glu | Gly | Tyr | Ala | Ala | Phe | Tyr | Cys | Asp | Gly |
|    |    |    |55  |    |    |    |    |60  |    |    |    |    |65  |    |    |

| Glu | Cys | Ser | Phe | Pro | Leu | Asn | Ala | His | Met | Asn | Ala | Thr | Asn | His | Ala |
|    |    |70  |    |    |    |    |75  |    |    |    |    |80  |    |    |    |

| Ile | Val | Gln | Thr | Leu | Val | His | Leu | Met | Phe | Pro | Asp | His | Val | Pro | Lys |

| | 85 | | | | 90 | | | | 95 | | | | 100 | |
|---|---|---|---|---|---|---|---|---|---|---|---|---|---|---|
| Pro | Cys | Cys | Ala | Pro | Thr | Lys | Leu | Asn | Ala | Ile | Ser | Val | Leu | Tyr | Phe |
| | | | | 105 | | | | | 110 | | | | | 115 | |
| Asp | Asp | Ser | Ser | Asn | Val | Ile | Leu | Lys | Lys | Tyr | Arg | Asn | Met | Val | Val |
| | | | 120 | | | | | 125 | | | | | 130 | | |
| Arg | Ser | Cys | Gly | Cys | His | | | | | | | | | | |
| | | 135 | | | | | | | | | | | | | |

( 2 ) INFORMATION FOR SEQ ID NO:11:

( i ) SEQUENCE CHARACTERISTICS:
        ( A ) LENGTH: 1003 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( F ) TISSUE TYPE: Human Heart ( v i i ) IMMEDIATE SOURCE:
        ( A ) LIBRARY: Human heart cDNA library stratagene catalog
            # 936208
        ( B ) CLONE: hH38

( v i i i ) POSITION IN GENOME:
        ( C ) UNITS: bp ( i x ) FEATURE:
        ( A ) NAME/KEY: CDS
        ( B ) LOCATION: 8..850

( i x ) FEATURE:
        ( A ) NAME/KEY: mat_peptide
        ( B ) LOCATION: 427..843

( i x ) FEATURE:
        ( A ) NAME/KEY: mRNA
        ( B ) LOCATION: 1..997

( x i ) SEQUENCE DESCRIPTION: SEQ ID NO:11:

| GAATTCC | GAG | CCC | CAT | TGG | AAG | GAG | TTC | CGC | TTT | GAC | CTG | ACC | CAG | ATC | 49 |
|---|---|---|---|---|---|---|---|---|---|---|---|---|---|---|---|
| | Glu | Pro | His | Trp | Lys | Glu | Phe | Arg | Phe | Asp | Leu | Thr | Gln | Ile | |
| | -139 | | | -135 | | | | | -130 | | | | | | |
| CCG | GCT | GGG | GAG | GCG | GTC | ACA | GCT | GCG | GAG | TTC | CGG | ATT | TAC | AAG | GTG | 97 |
| Pro | Ala | Gly | Glu | Ala | Val | Thr | Ala | Ala | Glu | Phe | Arg | Ile | Tyr | Lys | Val |
| -125 | | | | -120 | | | | | -115 | | | | | -110 | |
| CCC | AGC | ATC | CAC | CTG | CTC | AAC | AGG | ACC | CTC | CAC | GTC | AGC | ATG | TTC | CAG | 145 |
| Pro | Ser | Ile | His | Leu | Leu | Asn | Arg | Thr | Leu | His | Val | Ser | Met | Phe | Gln |
| | | | | -105 | | | | | -100 | | | | | -95 | |
| GTG | GTC | CAG | GAG | CAG | TCC | AAC | AGG | GAG | TCT | GAC | TTG | TTC | TTT | TTG | GAT | 193 |
| Val | Val | Gln | Glu | Gln | Ser | Asn | Arg | Glu | Ser | Asp | Leu | Phe | Phe | Leu | Asp |
| | | | -90 | | | | | -85 | | | | | -80 | | |
| CTT | CAG | ACG | CTC | CGA | GCT | GGA | GAC | GAG | GGC | TGG | CTG | GTG | CTG | GAT | GTC | 241 |
| Leu | Gln | Thr | Leu | Arg | Ala | Gly | Asp | Glu | Gly | Trp | Leu | Val | Leu | Asp | Val |
| | | -75 | | | | | -70 | | | | | -65 | | | |
| ACA | GCA | GCC | AGT | GAC | TGC | TGG | TTG | CTG | AAG | CGT | CAC | AAG | GAC | CTG | GGA | 289 |
| Thr | Ala | Ala | Ser | Asp | Cys | Trp | Leu | Leu | Lys | Arg | His | Lys | Asp | Leu | Gly |
| | -60 | | | | -55 | | | | | -50 | | | | | |
| CTC | CGC | CTC | TAT | GTG | GAG | ACT | GAG | GAT | GGG | CAC | AGC | GTG | GAT | CCT | GGC | 337 |
| Leu | Arg | Leu | Tyr | Val | Glu | Thr | Glu | Asp | Gly | His | Ser | Val | Asp | Pro | Gly |
| -45 | | | | | -40 | | | | | -35 | | | | | -30 |
| CTG | GCC | GGC | CTG | CTG | GGT | CAA | CGG | GCC | CCA | CGC | TCC | CAA | CAG | CCT | TTC | 385 |

```
Leu  Ala  Gly  Leu  Leu  Gly  Gln  Arg  Ala  Pro  Arg  Ser  Gln  Gln  Pro  Phe
          -25                      -20                          -15

GTG  GTC  ACT  TTC  TTC  AGG  GCC  AGT  CCG  AGT  CCC  ATC  CGC  ACC  CCT  CGG    433
Val  Val  Thr  Phe  Phe  Arg  Ala  Ser  Pro  Ser  Pro  Ile  Arg  Thr  Pro  Arg
              -10                       -5                         1

GCA  GTG  AGG  CCA  CTG  AGG  AGG  AGG  CAG  CCG  AAG  AAA  AGC  AAC  GAG  CTG    481
Ala  Val  Arg  Pro  Leu  Arg  Arg  Arg  Gln  Pro  Lys  Lys  Ser  Asn  Glu  Leu
      5                        10                      15

CCG  CAG  GCC  AAC  CGA  CTC  CCA  GGG  ATC  TTT  GAT  GAC  GTC  CAC  GGC  TCC    529
Pro  Gln  Ala  Asn  Arg  Leu  Pro  Gly  Ile  Phe  Asp  Asp  Val  His  Gly  Ser
20                            25                      30                      35

CAC  GGC  CGG  CAG  GTC  TGC  CGT  CGG  CAC  GAG  CTC  TAC  GTC  AGC  TTC  CAG    577
His  Gly  Arg  Gln  Val  Cys  Arg  Arg  His  Glu  Leu  Tyr  Val  Ser  Phe  Gln
               40                       45                           50

GAC  CTT  GGC  TGG  CTG  GAC  TGG  GTC  ATC  GCC  CCC  CAA  GGC  TAC  TCA  GCC    625
Asp  Leu  Gly  Trp  Leu  Asp  Trp  Val  Ile  Ala  Pro  Gln  Gly  Tyr  Ser  Ala
               55                       60                           65

TAT  TAC  TGT  GAG  GGG  GAG  TGC  TCC  TTC  CCG  CTG  GAC  TCC  TGC  ATG  AAC    673
Tyr  Tyr  Cys  Glu  Gly  Glu  Cys  Ser  Phe  Pro  Leu  Asp  Ser  Cys  Met  Asn
          70                       75                           80

GCC  ACC  AAC  CAC  GCC  ATC  CTG  CAG  TCC  CTG  GTG  CAC  CTG  ATG  AAG  CCA    721
Ala  Thr  Asn  His  Ala  Ile  Leu  Gln  Ser  Leu  Val  His  Leu  Met  Lys  Pro
     85                            90                      95

AAC  GCA  GTC  CCC  AAG  GCG  TGC  TGT  GCA  CCC  ACC  AAG  CTG  AGC  GCC  ACC    769
Asn  Ala  Val  Pro  Lys  Ala  Cys  Cys  Ala  Pro  Thr  Lys  Leu  Ser  Ala  Thr
100                      105                      110                      115

TCT  GTG  CTC  TAC  TAT  GAC  AGC  AGC  AAC  AAC  GTC  ATC  CTG  CGC  AAG  CAC    817
Ser  Val  Leu  Tyr  Tyr  Asp  Ser  Ser  Asn  Asn  Val  Ile  Leu  Arg  Lys  His
                    120                       125                      130

CGC  AAC  ATG  GTG  GTC  AAG  GCC  TGC  GGC  TGC  CAC  TGAGTCAGCC CGCCCAGCCC      870
Arg  Asn  Met  Val  Val  Lys  Ala  Cys  Gly  Cys  His
               135                       140

TACTGCAGCC ACCCTTCTCA TCTGGATCGG GCCCTGCAGA GGCAGAAAAC CCTTAAATGC                930

TGTCACAGCT CAAGCAGGAG TGTCAGGGGC CCTCACTCTC GGTGCCTACT TCCTGTCAGG                990

CTTCTGGGAA TTC                                                                  1003
```

(2) INFORMATION FOR SEQ ID NO:12:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:12:

```
Glu  Pro  His  Trp  Lys  Glu  Phe  Arg  Phe  Asp  Leu  Thr  Gln  Ile  Pro  Ala
-139                -135                      -130                      -125

Gly  Glu  Ala  Val  Thr  Ala  Ala  Glu  Phe  Arg  Ile  Tyr  Lys  Val  Pro  Ser
               -120                       -115                     -110

Ile  His  Leu  Leu  Asn  Arg  Thr  Leu  His  Val  Ser  Met  Phe  Gln  Val  Val
          -105                       -100                     -95

Gln  Glu  Gln  Ser  Asn  Arg  Glu  Ser  Asp  Leu  Phe  Phe  Leu  Asp  Leu  Gln
     -90                       -85                      -80

Thr  Leu  Arg  Ala  Gly  Asp  Glu  Gly  Trp  Leu  Val  Leu  Asp  Val  Thr  Ala
-75                       -70                      -65                      -60

Ala  Ser  Asp  Cys  Trp  Leu  Leu  Lys  Arg  His  Lys  Asp  Leu  Gly  Leu  Arg
               -55                       -50                      -45
```

| Leu | Tyr | Val | Glu | Thr | Glu | Asp | Gly | His | Ser | Val | Asp | Pro | Gly | Leu | Ala |
| | | -40 | | | | | -35 | | | | | -30 | | | |

| Gly | Leu | Leu | Gly | Gln | Arg | Ala | Pro | Arg | Ser | Gln | Gln | Pro | Phe | Val | Val |
| | | -25 | | | | -20 | | | | | | -15 | | | |

| Thr | Phe | Phe | Arg | Ala | Ser | Pro | Ser | Pro | Ile | Arg | Thr | Pro | Arg | Ala | Val |
| | -10 | | | | | -5 | | | | | 1 | | | | 5 |

| Arg | Pro | Leu | Arg | Arg | Arg | Gln | Pro | Lys | Lys | Ser | Asn | Glu | Leu | Pro | Gln |
| | | | | 10 | | | | | 15 | | | | | 20 | |

| Ala | Asn | Arg | Leu | Pro | Gly | Ile | Phe | Asp | Asp | Val | His | Gly | Ser | His | Gly |
| | | | 25 | | | | | 30 | | | | | 35 | | |

| Arg | Gln | Val | Cys | Arg | Arg | His | Glu | Leu | Tyr | Val | Ser | Phe | Gln | Asp | Leu |
| | | 40 | | | | | 45 | | | | | 50 | | | |

| Gly | Trp | Leu | Asp | Trp | Val | Ile | Ala | Pro | Gln | Gly | Tyr | Ser | Ala | Tyr | Tyr |
| | 55 | | | | | 60 | | | | | 65 | | | | |

| Cys | Glu | Gly | Glu | Cys | Ser | Phe | Pro | Leu | Asp | Ser | Cys | Met | Asn | Ala | Thr |
| 70 | | | | | 75 | | | | | 80 | | | | | 85 |

| Asn | His | Ala | Ile | Leu | Gln | Ser | Leu | Val | His | Leu | Met | Lys | Pro | Asn | Ala |
| | | | | 90 | | | | | 95 | | | | | 100 | |

| Val | Pro | Lys | Ala | Cys | Cys | Ala | Pro | Thr | Lys | Leu | Ser | Ala | Thr | Ser | Val |
| | | | 105 | | | | | 110 | | | | | 115 | | |

| Leu | Tyr | Tyr | Asp | Ser | Ser | Asn | Asn | Val | Ile | Leu | Arg | Lys | His | Arg | Asn |
| | | 120 | | | | | 125 | | | | | 130 | | | |

| Met | Val | Val | Lys | Ala | Cys | Gly | Cys | His |
| | 135 | | | | | 140 | | |

(2) INFORMATION FOR SEQ ID NO:13:

( i ) SEQUENCE CHARACTERISTICS:
        ( A ) LENGTH: 3623 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: pALBP2-781

( i x ) FEATURE:
        ( A ) NAME/KEY: CDS
        ( B ) LOCATION: 2724..3071

( i x ) FEATURE:
        ( A ) NAME/KEY: terminator
        ( B ) LOCATION: 3150..3218

( i x ) FEATURE:
        ( A ) NAME/KEY: RBS
        ( B ) LOCATION: 2222..2723

( x i ) SEQUENCE DESCRIPTION: SEQ ID NO:13:

```
GACGAAAGGG   CCTCGTGATA   CGCCTATTTT   TATAGGTTAA   TGTCATGATA   ATAATGGTTT        60

CTTAGACGTC   AGGTGGCACT   TTTCGGGGAA   ATGTGCGCGG   AACCCCTATT   TGTTTATTTT       120

TCTAAATACA   TTCAAATATG   TATCCGCTCA   TGAGACAATA   ACCCTGATAA   ATGCTTCAAT       180

AATATTGAAA   AAGGAAGAGT   ATGAGTATTC   AACATTTCCG   TGTCGCCCTT   ATTCCCTTTT       240

TTGCGGCATT   TTGCCTTCCT   GTTTTGCTC    ACCCAGAAAC   GCTGGTGAAA   GTAAAAGATG       300

CTGAAGATCA   GTTGGGTGCA   CGAGTGGGTT   ACATCGAACT   GGATCTCAAC   AGCGGTAAGA       360

TCCTTGAGAG   TTTTCGCCCC   GAAGAACGTT   TTCCAATGAT   GAGCACTTTT   AAAGTTCTGC       420

TATGTGGCGC   GGTATTATCC   CGTATTGACG   CCGGGCAAGA   GCAACTCGGT   CGCCGCATAC       480
```

-continued

```
ACTATTCTCA GAATGACTTG GTTGAGTACT CACCAGTCAC AGAAAAGCAT CTTACGGATG    540
GCATGACAGT AAGAGAATTA TGCAGTGCTG CCATAACCAT GAGTGATAAC ACTGCGGCCA    600
ACTTACTTCT GACAACGATC GGAGGACCGA AGGAGCTAAC CGCTTTTTTG CACAACATGG    660
GGGATCATGT AACTCGCCTT GATCGTTGGG AACCGGAGCT GAATGAAGCC ATACCAAACG    720
ACGAGCGTGA CACCACGATG CCTGTAGCAA TGGCAACAAC GTTGCGCAAA CTATTAACTG    780
GCGAACTACT TACTCTAGCT TCCCGGCAAC AATTAATAGA CTGGATGGAG GCGGATAAAG    840
TTGCAGGACC ACTTCTGCGC TCGGCCCTTC CGGCTGGCTG GTTATTGCT GATAAATCTG     900
GAGCCGGTGA GCGTGGGTCT CGCGGTATCA TTGCAGCACT GGGGCCAGAT GGTAAGCCCT    960
CCCGTATCGT AGTTATCTAC ACGACGGGGA GTCAGGCAAC TATGGATGAA CGAAATAGAC   1020
AGATCGCTGA GATAGGTGCC TCACTGATTA AGCATTGGTA ACTGTCAGAC CAAGTTTACT   1080
CATATATACT TTAGATTGAT TTAAAACTTC ATTTTTAATT TAAAGGATC TAGGTGAAGA    1140
TCCTTTTTGA TAATCTCATG ACCAAAATCC CTTAACGTGA GTTTCGTTC CACTGAGCGT    1200
CAGACCCCGT AGAAAAGATC AAAGGATCTT CTTGAGATCC TTTTTTTCTG CGCGTAATCT   1260
GCTGCTTGCA AACAAAAAAA CCACCGCTAC CAGCGGTGGT TTGTTTGCCG GATCAAGAGC   1320
TACCAACTCT TTTTCCGAAG GTAACTGGCT TCAGCAGAGC GCAGATACCA AATACTGTCC   1380
TTCTAGTGTA GCCGTAGTTA GGCCACCACT TCAAGAACTC TGTAGCACCG CCTACATACC   1440
TCGCTCTGCT AATCCTGTTA CCAGTGGCTG CTGCCAGTGG CGATAAGTCG TGTCTTACCG   1500
GGTTGGACTC AAGACGATAG TTACCGGATA AGGCGCAGCG GTCGGGCTGA ACGGGGGTT    1560
CGTGCACACA GCCCAGCTTG GAGCGAACGA CCTACACCGA ACTGAGATAC CTACAGCGTG   1620
AGCATTGAGA AAGCGCCACG CTTCCCGAAG GGAGAAAGGC GGACAGGTAT CCGGTAAGCG   1680
GCAGGGTCGG AACAGGAGAG CGCACGAGGG AGCTTCCAGG GGGAAACGCC TGGTATCTTT   1740
ATAGTCCTGT CGGGTTTCGC CACCTCTGAC TTGAGCGTCG ATTTTGTGA TGCTCGTCAG    1800
GGGGGCGGAG CCTATGGAAA AACGCCAGCA ACGCGGCCTT TTTACGGTTC CTGGCCTTTT   1860
GCTGGCCTTT TGCTCACATG TTCTTTCCTG CGTTATCCCC TGATTCTGTG GATAACCGTA   1920
TTACCGCCTT TGAGTGAGCT GATACCGCTC GCCGCAGCCG AACGACCGAG CGCAGCGAGT   1980
CAGTGAGCGA GGAAGCGGAA GAGCGCCCAA TACGCAAACC GCCTCTCCCC GCGCGTTGGC   2040
CGATTCATTA ATGCAGAATT GATCTCTCAC CTACCAAATA ATGCCCCCCT GCAAAAAATA   2100
AATTCATATA AAAAACATAC AGATAACCAT CTGCGGTGAT AAATTATCTC TGGCGGTGTT   2160
GACATAAATA CCACTGGCGG TGATACTGAG CACATCAGCA GGACGCACTG ACCACCATGA   2220
AGGTGACGCT CTTAAAAATT AAGCCCTGAA GAAGGGCAGC ATTCAAAGCA GAAGGCTTTG   2280
GGGTGTGTGA TACGAAACGA AGCATTGGCC GTAAGTGCGA TTCCGGATTA GCTGCCAATG   2340
TGCCAATCGC GGGGGGTTTT CGTTCAGGAC TACAACTGCC ACACACCACC AAAGCTAACT   2400
GACAGGAGAA TCCAGATGGA TGCACAAACA CGCCGCCGCG AACGTCGCGC AGAGAAACAG   2460
GCTCAATGGA AAGCAGCAAA TCCCCTGTTG GTTGGGGTAA GCGCAAAACC AGTTCCGAAA   2520
GATTTTTTTA ACTATAAACG CTGATGGAAG CGTTTATGCG GAAGAGGTAA AGCCCTTCCC   2580
GAGTAACAAA AAAACAACAG CATAAATAAC CCCGCTCTTA CACATTCCAG CCCTGAAAAA   2640
GGGCATCAAA TTAAACCACA CCTATGGTGT ATGCATTTAT TTGCATACAT TCAATCAATT   2700
GTTATCTAAG GAAATACTTA CAT ATG CAA GCT AAA CAT AAA CAA CGT AAA       2750
                       Met Gln Ala Lys His Lys Gln Arg Lys
                       1                 5
```

| | | | | | | | | | | | | | | | | |
|---|---|---|---|---|---|---|---|---|---|---|---|---|---|---|---|---|
| CGT | CTG | AAA | TCT | AGC | TGT | AAG | AGA | CAC | CCT | TTG | TAC | GTG | GAC | TTC | AGT | 2798 |
| Arg | Leu | Lys | Ser | Ser | Cys | Lys | Arg | His | Pro | Leu | Tyr | Val | Asp | Phe | Ser | |
| 10 | | | | 15 | | | | | 20 | | | | | 25 | | |
| GAC | GTG | GGG | TGG | AAT | GAC | TGG | ATT | GTG | GCT | CCC | CCG | GGG | TAT | CAC | GCC | 2846 |
| Asp | Val | Gly | Trp | Asn | Asp | Trp | Ile | Val | Ala | Pro | Pro | Gly | Tyr | His | Ala | |
| | | | | 30 | | | | | 35 | | | | | 40 | | |
| TTT | TAC | TGC | CAC | GGA | GAA | TGC | CCT | TTT | CCT | CTG | GCT | GAT | CAT | CTG | AAC | 2894 |
| Phe | Tyr | Cys | His | Gly | Glu | Cys | Pro | Phe | Pro | Leu | Ala | Asp | His | Leu | Asn | |
| | | | 45 | | | | | 50 | | | | | 55 | | | |
| TCC | ACT | AAT | CAT | GCC | ATT | GTT | CAG | ACG | TTG | GTC | AAC | TCT | GTT | AAC | TCT | 2942 |
| Ser | Thr | Asn | His | Ala | Ile | Val | Gln | Thr | Leu | Val | Asn | Ser | Val | Asn | Ser | |
| | | 60 | | | | | 65 | | | | | 70 | | | | |
| AAG | ATT | CCT | AAG | GCA | TGC | TGT | GTC | CCG | ACA | GAA | CTC | AGT | GCT | ATC | TCG | 2990 |
| Lys | Ile | Pro | Lys | Ala | Cys | Cys | Val | Pro | Thr | Glu | Leu | Ser | Ala | Ile | Ser | |
| | 75 | | | | | 80 | | | | | 85 | | | | | |
| ATG | CTG | TAC | CTT | GAC | GAG | AAT | GAA | AAG | GTT | GTA | TTA | AAG | AAC | TAT | CAG | 3038 |
| Met | Leu | Tyr | Leu | Asp | Glu | Asn | Glu | Lys | Val | Val | Leu | Lys | Asn | Tyr | Gln | |
| 90 | | | | | 95 | | | | | 100 | | | | | 105 | |
| GAC | ATG | GTT | GTG | GAG | GGT | TGT | GGG | TGT | CGC | TAGTACAGCA | | AAATTAAATA | | | | 3088 |
| Asp | Met | Val | Val | Glu | Gly | Cys | Gly | Cys | Arg | | | | | | | |
| | | | | 110 | | | | | 115 | | | | | | | |

| | | | | |
|---|---|---|---|---|
| CATAAATATA | TATATATATA | TATATTTTAG | AAAAAAGAAA | AAAATCTAGA GTCGACCTGC | 3148 |
| AGTAATCGTA | CAGGGTAGTA | CAAATAAAAA | AGGCACGTCA | GATGACGTGC CTTTTTTCTT | 3208 |
| GTGAGCAGTA | AGCTTGGCAC | TGGCCGTCGT | TTTACAACGT | CGTGACTGGG AAAACCCTGG | 3268 |
| CGTTACCCAA | CTTAATCGCC | TTGCAGCACA | TCCCCCTTTC | GCCAGCTGGC GTAATAGCGA | 3328 |
| AGAGGCCCGC | ACCGATCGCC | CTTCCCAACA | GTTGCGCAGC | CTGAATGGCG AATGGCGCCT | 3388 |
| GATGCGGTAT | TTTCTCCTTA | CGCATCTGTG | CGGTATTTCA | CACCGCATAT ATGGTGCACT | 3448 |
| CTCAGTACAA | TCTGCTCTGA | TGCCGCATAG | TTAAGCCAGC | CCGACACCC GCCAACACCC | 3508 |
| GCTGACGCGC | CCTGACGGGC | TTGTCTGCTC | CCGGCATCCG | CTTACAGACA AGCTGTGACC | 3568 |
| GTCTCCGGGA | GCTGCATGTG | TCAGAGGTTT | TCACCGTCAT | CACCGAAACG CGCGA | 3623 |

( 2 ) INFORMATION FOR SEQ ID NO:14:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | | |
|---|---|---|---|---|---|---|---|---|---|---|---|---|---|---|---|
| Met | Gln | Ala | Lys | His | Lys | Gln | Arg | Lys | Arg | Leu | Lys | Ser | Ser | Cys | Lys |
| 1 | | | | 5 | | | | | 10 | | | | | 15 | |
| Arg | His | Pro | Leu | Tyr | Val | Asp | Phe | Ser | Asp | Val | Gly | Trp | Asn | Asp | Trp |
| | | | 20 | | | | | 25 | | | | | 30 | | |
| Ile | Val | Ala | Pro | Pro | Gly | Tyr | His | Ala | Phe | Tyr | Cys | His | Gly | Glu | Cys |
| | | 35 | | | | | 40 | | | | | 45 | | | |
| Pro | Phe | Pro | Leu | Ala | Asp | His | Leu | Asn | Ser | Thr | Asn | His | Ala | Ile | Val |
| | 50 | | | | | 55 | | | | | 60 | | | | |
| Gln | Thr | Leu | Val | Asn | Ser | Val | Asn | Ser | Lys | Ile | Pro | Lys | Ala | Cys | Cys |
| 65 | | | | | 70 | | | | | 75 | | | | | 80 |
| Val | Pro | Thr | Glu | Leu | Ser | Ala | Ile | Ser | Met | Leu | Tyr | Leu | Asp | Glu | Asn |
| | | | | 85 | | | | | 90 | | | | | 95 | |
| Glu | Lys | Val | Val | Leu | Lys | Asn | Tyr | Gln | Asp | Met | Val | Val | Glu | Gly | Cys |
| | | | 100 | | | | | 105 | | | | | 110 | | |

Gly Cys Arg
     115

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CATGGGCAGC TCGAG     15

( 2 ) INFORMATION FOR SEQ ID NO:16:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GAGGGTTGTG GGTGTCGCTA GTGAGTCGAC TACAGCAAAAT T     42

( 2 ) INFORMATION FOR SEQ ID NO:17:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGATGTGGGT GCCGCTGACT CTAGAGTCGA CGGAATTC     38

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AATTCACCAT GATTCCTGGT AACCGAATGC T     31

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CATTC GGTTACCAGG AATCATGGTG     25

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CGACCTGCAG CCACCATGCATCT GACTGTA 30

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

TGCCTGCAGT TTAATATTAG TGGCAGC 27

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

CGACCTGCAG CCACC 15

( 2 ) INFORMATION FOR SEQ ID NO:23:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TCGACCCACC ATGCCGGGGC TGGGGCGGAG GGCGCAGTGG CTGTGCTGGT GGTGGGGGCT 60

GTGCTGCAGC TGCTGCGGGC C 81

( 2 ) INFORMATION FOR SEQ ID NO:24:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CGCAGCAGCT GCACAGCAGC CCCCACCACC AGCACAGCCA CTGCGCCCTC CGCCCCAGCC 60

CCGGCATGGT GGG 73

(2) INFORMATION FOR SEQ ID NO:25:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TCGACTGGTT T                                              11

(2) INFORMATION FOR SEQ ID NO:26:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CGAAACCAG                                               9

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TCGACAGGCT CGCCTGCA                               18

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GGCGAGCCTG                                              10

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CAGGTCGACC CACCATGCAC GTGCGCTCA                 29

(2) INFORMATION FOR SEQ ID NO:30:

(i) SEQUENCE CHARACTERISTICS:
        (A) LENGTH: 27 base pairs

-continued (B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:30:

TCTGTCGACC TCGGAGGAGC TAGTGGC      27